US007419948B2

(12) United States Patent
Velander et al.

(10) Patent No.: US 7,419,948 B2
(45) Date of Patent: Sep. 2, 2008

(54) TREATMENT OF HEMOPHILIA WITH HUMAN FACTOR IX PRODUCED IN MAMMARY TISSUE OF TRANSGENIC MAMMALS

(75) Inventors: William H. Velander, Blacksburg, VA (US); William N. Drohan, Springfield, VA (US); Henryk Lubon, Rockville, MD (US); John L. Johnson, deceased, late of Blacksburg VA (US); by Mary Ann H. Johnson, legal representative, Blacksburg, VA (US)

(73) Assignees: American Red Cross, Rockville, MD (US); Virginia Tech Intellectual Properties, Inc., Blacksburg, VA (US)

( * ) Notice: Subject to any disclaimer, the term of this patent is extended or adjusted under 35 U.S.C. 154(b) by 88 days.

(21) Appl. No.: 11/117,705

(22) Filed: Apr. 29, 2005

(65) Prior Publication Data

US 2006/0287228 A1 Dec. 21, 2006

Related U.S. Application Data

(60) Continuation of application No. 10/062,447, filed on Feb. 5, 2002, now abandoned, which is a division of application No. 09/367,087, filed as application No. PCT/US98/02638 on Feb. 13, 1998, now Pat. No. 6,344,596.

(60) Provisional application No. 60/037,145, filed on Feb. 14, 1997.

(51) Int. Cl.
*A61K 38/00* (2006.01)
*A61K 35/14* (2006.01)
*C12P 21/00* (2006.01)

(52) U.S. Cl. .............................. 512/12; 800/7; 530/381
(58) Field of Classification Search .................. 530/381; 424/12; 435/212
See application file for complete search history.

(56) References Cited

U.S. PATENT DOCUMENTS

| 4,786,726 A | 11/1988 | Smith |
| 4,873,316 A | 10/1989 | Meade et al. |
| 5,171,569 A | 12/1992 | Ansons et al. |
| 5,322,775 A | 6/1994 | Clark et al. |
| 5,366,894 A | 11/1994 | Clark et al. |
| 5,476,995 A | 12/1995 | Clark et al. |
| 5,589,604 A | 12/1996 | Drohan et al. |
| 5,831,141 A | 11/1998 | Lubon et al. |

FOREIGN PATENT DOCUMENTS

| EP | 0 451 823 | 10/1991 |
| EP | 0 791 652 A1 | 8/1997 |
| EP | 0 274 489 B1 | 10/1997 |
| EP | 0 396 699 B1 | 10/1997 |
| GB | 2 125 409 | 3/1984 |
| WO | WO 90/05188 | 5/1990 |
| WO | WO 91/08216 | 6/1991 |
| WO | WO 94/05796 | 3/1994 |
| WO | WO 95/30000 | 11/1995 |

OTHER PUBLICATIONS

Kim et al. Purified Factor IX Using Monoclonal Immunoaffinity Technique: Clinical Trials in Hemophilia B and Comparison to Prothrombin Complex Concentrates. Blood. Feb. 1, 1992, vol. 79, No. 3, pp. 568-575.*

Clark, et al. "Expression of Human Anti-Hemophilic Factor IX in the Milk of Transgenic Sheep," Bio/Technology, vol. 7, pp. 487-492 (1989).

Velander, et al. Proc. Natl. Acad. Sci. 89, 12003-12007 (1992).

Drohan, et al. Transgenic Res. 3, 355-364 (1994).

Anson, et al. Nature 315, 683-685 (1985).

Yull, et al. "Fixing human factor IX (fIX): Correction of cryptic RNA splice enables the production of biologically active fIX in the mammary gland of transgenic mice," Proc. Natl. Acad. Sci., vol. 92, 10899-10903 (1995).

Morcol, et al., "The Porcine Mammary Glad as a Bioreactor for Complex Proteins," Annals of the New York Academy of Sciences (1994), vol. 721, pp. 218-233.

Wright, et al. "High Level Expression of Active Human Alpha-1-Antitrypsin in the Milk of Transgenic Sheep," Bio/Technology (1991), vol. 9, pp. 830-834.

Wall, "Transgenic Livestock: Progress and Prospects for the Future," Theriogenology (1996), vol. 45, pp. 57-68.

(Continued)

*Primary Examiner*—Deborah Crouch
(74) *Attorney, Agent, or Firm*—Cooley Godward Kronish, LLP

(57) ABSTRACT

Recombinant Factor IX characterized by a high percentage of active protein can be obtained in the milk of transgenic animals that incorporate chimeric DNA molecules according to the present invention. Transgenic animals of the present invention are produced by introducing into developing embryos DNA that encodes Factor IX, such that the foreign DNA is stably incorporated in the DNA of germ line cells of the mature animal. Particularly efficient expression was accomplished using a chimeric construct comprising a mammary gland specific promoter, Factor IX cDNA that lacked the complete or any portion of the 5'-untranslated and 3'-untranslated region, which is substituted with a 5-' and 3'-end of the mouse whey acidic protein gene. In vitro cell cultures of cells explanted from the transgenic mammal of the invention and methods of producing Factor IX from such said culture and methods of treating hemophilia B are also described.

13 Claims, 9 Drawing Sheets

OTHER PUBLICATIONS

Massoud et al., "The deleterious effects of human erythropoietin gene driven by the rabbit whey acidic protein gene promoter in transgenic rabbits," Reprod. Nutr. Dev. (1996), vol. 36, pp. 555-563.

Kim et al., "Purified Factor IX Using Monoclonal Immunoaffinity Technique: Clinical Trials in Hemophilia B and Comparison to Prothrombin Complex Concentrates," Blood (1992), vol. 79, No. 3, pp. 568-575.

Aguirre et al., "Expression of human erythroporetin transgenes and of the endogenous wap gene in the mammary gland of transgenic rabbits during gestation and lactation," Transgenic Research, vol. 7 (1998), pp. 311-317.

* cited by examiner

TREATMENT OF HEMOPHILIA WITH HUMAN FACTOR IX PRODUCED IN MAMMARY TISSUE OF TRANSGENIC MAMMALS

CROSS-REFERENCE TO RELATED PATENT APPLICATIONS

This application is a continuation of U.S. patent application Ser. No. 10/062,447, now abandoned, filed on Feb. 5, 2002, which is a division of application Ser. No. 09/367,087, filed on Sep. 15, 1999, now Pat. No. 6,344,596, which claims benefit of PCT/US98/02638, filed on Feb. 13, 1998, which claims benefit of 60/037,145 filed on Feb. 14, 1997, all of which are incorporated herein by reference in their entirety.

BACKGROUND OF THE INVENTION

1. Field of the Invention

The present invention relates to the production of natural and modified forms of Factor IX. In particular, the invention relates to a transgenic animal containing, stably incorporated in its genomic DNA, an exogenous Factor IX gene that is expressed specifically in mammary tissue, such that Factor IX is secreted into milk produced by the animal. In particular, the invention relates to the production of human Factor IX in the milk of a transgenic non-human mammal using a DNA molecule that comprises a whey acidic protein promoter gene, 5' regulatory sequences containing the promoter, human Factor IX cDNA that lacks at least a portion of the complete or any portion of or the complete the 3'-untranslated region of the native human Factor IX gene, but contains the 5' and 3-untranslated region of the mouse whey acidic protein gene.

2. Background

Human Factor IX, or "Christmas factor," is encoded by a single-copy gene residing on the X-chromosome at q27.1. For a review of Factor IX gene structure and expression, see High et al., "Factor IX," in MOLECULAR BASIS OF THROMBOSIS AND HEMOSTASIS, High (ed.), pages 215-237 (Dekker 1995); Kurachi et al., Thromb. Haemost. 73:333 (1995). The Factor IX gene is at least 34 kilobase (kb) pairs in size, and it is composed of eight exons. The major transcription start site of the Factor IX gene in human liver is located at about nucleotide −176. The human Factor IX mRNA is composed of 205 bases for the 5' untranslated region, 1383 bases for the prepro Factor IX, a stop codon and 1392 bases for the 3' untranslated region.

Factor IX is synthesized as a prepropolypetide chain composed of three domains: a signal peptide of 29 amino acids, a propeptide of 17 amino acids, which is required for γ-carboxylation of glutamic acid residues, and a mature Factor IX protein of 415 amino acid residues. The Factor IX zymogen undergoes three types of post-translational modifications before it is secreted into the blood: a vitamin K-dependent conversion of glutamic acid residues to carboxyglutamic acids, addition of hydrocarbon chains, and β-hydroxylation of an aspartic acid. Mature Factor IX protein contains 12 γ-carboxylated glutamic acid (Gla) residues. Due to the requirement of vitamin K by γ-carboxylase, Factor IX is one of several vitamin K-dependent blood coagulation factors.

The activation of Factor IX is achieved by a two-step removal of the activation peptide ($Ala^{146}$-$Arg^{180}$) from the molecule. Bajaj et al., "Human factor IX and factor IXa," in METHODS IN ENZYMOLOGY (1993). The first cleavage is made at the $Arg^{145}$-$Ala^{146}$ site by either Factor XIa or Factor VIIa/tissue factor. The second, and rate limiting cleavage is made at $Arg^{180}$-$Val^{181}$. The activation pathways involving Factor XIa and Factor VIIa/tissue factor are both calcium-dependent. However, the Factor VIIa/tissue factor pathway requires tissue factor that is released from damaged endothelial cells. Activated human Factor IX thus exists as a disulfide linked heterodimer of the heavy chain and light chain. For full biological activity, human Factor IX must also have the propeptide removed and must be fully γ-carboxylated. Kurachi et al., Blood Coagulation and Fibrinolysis 4:953 (1993).

Factor IX is the precursor of a serine protease required for blood clotting by the intrinsic clotting pathway. Defects in Factor IX synthesis result in hemophilia B (or Christmas disease), an X-linked disorder that occurs in about one in 30,000 males. Patients with hemophilia B are treated with Factor IX obtained from pooled plasma from normal individuals. Martinowitz et al., Acta Haematol 94(Suppl. 1):35 (1995). Such Factor IX preparations, however, may be pyrogenic and may be contaminated with pathogenic agents or viruses. Accordingly, it would be advantageous to develop a means to prepare purified Factor IX that did not require extraction from human plasma.

In the past, therapeutic proteins have been produced in E. coli. However, limitations in secretion and post-translational modification which occur in all living cells has rendered recombinant protein production a highly species, tissue and cell specific phenomena. In an example of recombinant FIX expression in mammalian cells, the populations of recombinant FIX produced in baby hamster kidney cells are not the same protein products as FIX produced in Chinese hamster ovary cells (Busby et al., Nature 316:684-686 (1985); Kaufman et al., J. Biol. Chem. 261: 9622-9628 (1986)). These proteins have profound differences in γ-carboxylation and propeptide removal and these differences have been established as being very important in determining biological activity. Most importantly, only less than about 40 milliunits/hr/ml of active rFIX were detected in CHO cells even after coexpression of the propeptide cleaving enzyme PACE, coexpression of the carboxylase enzyme, and extensive gene amplification with methotrexate in an attempt to increase expression level and activity (Wasley et al. J. Biol. Chem. 268: 8458-8465 (1993); Rehemtulla et al., Proc. Natl. Acad. Sci. (USA), 90: 4611-4615 (1993)). Researchers concluded that multiple limitations in the secretion of active rFIX exist in mammalian cells (Rehemtulla et al., 1993) and that the problem of gene transcription was secondary and indeed trivial with respect to post-translational processing of biologically active rFIX in mammalian cells. Thus, FIX mRNA splicing is a species specific effect occurring in mice and perhaps sheep, but not pigs. Although one might hypothesize that a FIX could be expressed, one could not predict with any certainty whether such product would be a clinically acceptable, practical, recombinant therapeutic FIX product for a given hemophiliac indication.

Production of recombinant Factor IX in mammalian cell culture (HepG2, mouse fibroblast, mouse hepatoma, rat hepatoma, BHK, CHO cells) repeatedly has been shown to be recalcitrant and cell-system specific with respect to intracellular restrictions on secretion and proteolytic processing, post-translational modification, expression levels, biological activity, downstream recovery from production media, and substantiation of circulation half-life (Busby et al., (1985); de la Salle et al. Nature 316: 268-270 (1985); Anson et al., Nature 315: 684-686 (1985); Rehemtulla et al., 1993; Wasley, et al., (1993); Kaufman et al., (1986); Jallat et al., EMBO J. 9: 3295-3301 (1990)). Importantly, the aforementioned works concluded that nontrivial improvements in these combined criteria are needed if a practical prophylactic FIX therapeutic product is to be made available from any recombinant mammalian cell production source. For example, attempts to increase the specific activity of rFIX produced by CHO cells by rectifying problems with under-carboxylation by co-expression of the vitamin K-dependent carboxylase enzyme resulted in no improvement in γ-carboxylation or biological activity (Rehemtulla et al., (1993), implying that multiple rate limitations in this post-translational modification exist.

Similar difficulties in the production of significant amounts of biologicaly active rFIX in the mammary epithelial cells of transgenic animals also has been documented in the literature. Although WO-A-90/05188 and WO-A-91-08216 predict that production of rFIX should be possible in their production systems, no data are presented in WO-A-91-08216, and only very low levels of secreted rFIX (25 ng/ml) with no biological activity were reported in transgenic sheep in WO-A 90/05188 and in related publications, (Clark et al., *Bio/Technology* 7: 487-4992 (1989)). Higher expression levels have recently been reported in the milk of sheep (5 μg/ml), but again, the product had no biological activity (Colman, *IBC Third International Symposium on Exploiting Transgenic Technology for Commercial Development*, San Diego, Calif. (1995)). This demonstrates that the polypeptides produced in WO-A-90/05188, Clark et al. (1989), and Colman (1995) were a different species than native human FIX with dissimilar biological activity to human FIX, and could never be used for therapeutic purposes. Work by Clark et al. (1992) stated that problems in synthesis of rFIX in the mammary gland of transgenic mice was the result of aberrant splicing of the rFIX mRNA in the 3' untranslated region. Correction of the aberrant splicing in transgenic mice has been demonstrated (Yull et al. *Proc. Natl. Acad. Sci. USA* 92: 10899-10903 (1995); Clark, et al. (1989), WO 95/30000)), resulting in higher expression levels (up to 61 μg/ml) with about 40% biological active material. However, this aberrant splicing phenomenon appears to be species- and tissue-specific in the mouse mammary gland; other reports with the 3' UTR sequences in CHO cell lines and in the liver of transgenic mice specifically show no evidence of aberrant splicing (Kaufman et al., (1986); Jallat et al., (1990)). In addition, no evidence was reported for aberrant mRNA splicing of FIX transcripts with 3' UTR sequences in a human hepatoma cell line (de la Salle et al., (1985)), a mouse fibroblast cell line (de la Salle et al., (1985)), a rat hepatoma cell line (Anson et al., 1985)), or a BHK cell line (Busby et al., (1985)). No data are presented to justify the prediction that the altered transgene of WO95/30000 will necessarily improve the secretion and biological activity of rFIX in the milk of transgenic livestock or any other cell line. Therefore the claims presented in WO 95/30000 are purely speculative and are limited to the mammary gland of transgenic mice.

The stability of the rFIX product in the milk of transgenic livestock during upstream and downstream processing is a critical issue for the production of a practical therapeutic. Data presented in Clark et al. (1989) showed that Clark's method of downstream recovery of what little rFIX was in the milk of their transgenic sheep was not reproducible: in one of the preparations, a significant amount of rFIX was proteolytically activated. The infusion of activated FIX (FIXa) into a patient is fatal (Kingdon et al., *Thrombosis, Diathes. Haemorrh.* (*Stuttg.*) 33: 617 (1975)). FIX can be activated by FXI and/or FVIIa/Tissue factor complex in the presence of calcium and phospholipids (Kurachi et al., *Blood Coagulation and Fibrinolysis* 4: 953-974 (1993)). Milk is a medium containing calcium and phospholipid surfaces. In addition, there is extensively conserved homology between mammalian blood coagulation factors, especially between porcine FXI and human FXI (Mashiko and Takahashi, *Biol. Chem. Hoppe-Seyler* 375: 481-484 (1994)). Detectable levels of porcine FVII(a) and FXI(a) in the milk of nontransgenic pigs, and elevated levels of FVII(a) and FXI(a) in the milk of a pig with mastitic milk have been measured. Thus, one could predict that the recovery of a useful unactivated rFIX produced in the milk of transgenic livestock will be very sensitive to the health of the mammary gland (i.e., no subclinical or clinical mastitis), to the milking procedure (i.e., no tissue damage), to pretreatment of the milk immediately after collection, to storage of the milk before processing, and to the purification and formulation process itself. One would also predict that the undesirable in vivo activation of rFIX also can be minimized by the coexpression of inhibitors to FVIIa/TF such as the Tissue Factor Pathway Inhibitor (TFPI) protein, also called LACI, or the hybrid protein FX-LACI which is also a known inhibitor to FVIIa/TF. Although specific inhibitors of FXIa have not been identified, a similar approach can be made for neutralizing FXIa activation by coexpression of analogues of polypeptide substrates of FXIa similar to those that are commercially available for amidolytic assays. Yet another strategy may be to overexpress rFIX at very high levels (>1 g/l milk) such that the FIX activating enzyme is extremely limiting. Otherwise, steps must be taken immediately after milk collection to minimize activation. These include, but are not limited to, chelation of calcium (e.g., addition of EDTA), phospholipid removal, adjustment of pH, storage in ultra-low freezers, controlled thawing procedures, addition of protease inhibitors, and purification procedures that maintain minimal activation conduciveness. If activated rFIX still persists in the purified product, removal can be facilitated by lectin chromatography(N-linked carbohydrate moieties exist only in the activation peptide), immunoaffinity chromatography using a Mab directed to the activation peptide, or by metal ion induced precipitation techniques that can select for the differences in molecular stability of unactivated vs. activated FIX. Because of these inherent difficulties in production of active FIX at sufficiently high levels in mammalian cells and transgenic livestock, gene therapy has been cited as perhaps a more practical way of achieving a prophylactic therapeutic rather than recombinant technology (Kurachi et al., (1993); Kay et al., *Proc. Natl. Acad. Sci. USA* 91: 2353-2357 (1994)); Fallaux et al., *Thromb-Haemost.* 74: 266-73 (1995)). This is certainly a profound reality because it specifically teaches a product suitable for FIX prophylaxis has not yet been found using recombinant production in mammalian cells, even those that have been shown to express active FIX, albeit at low levels. The best recombinant FIX cell production system made from CHO cells is produced at low secretion levels (Rehemtulla et al., (1993)) and is in fact not suitable for prophylaxis. Furthermore, the data have shown that the homologous plasma proteins. FIX and protein C all have very different, cell-specific restrictions on post-translational processing, proteolytic processing, and secretion which preclude on a protein-specific basis the predictability of high expression levels, biological activity, downstream recovery from production media, and predictable circulation half-life (Grinnell et al., "Native and Modified recombinant human protein C: function, secretion, and postranslational modifications," In *Protein C and Related Anticoagulants, eds*. D. F. Bruley and Drohan 29-63, Gulf Publishing Co., Houston, Tex. (1990); Yan et al., *Trends in Biochem. Sci.* (1989); Busby et al., (1985)).

Therefore, a need still exists for a means to obtain significant amounts of purified Factor IX from a source other than human plasma. A need also exists for a practical means for producing in mammalian cells rFIX, which is suitable as a treatment for hemophilia B.

SUMMARY OF THE INVENTION

Accordingly, it is an object of the present invention to provide a method for producing a transgenic animal that secretes biologically human active Factor IX into its milk.

It is a further object of this invention to provide a transgenic animal that produces at least 100 μg of human Factor IX per milliliter of milk.

These and other objects are achieved, in accordance with one embodiment of the present invention by the provision of a transgenic non-human mammal containing an exogenous DNA molecule stably integrated in its genome.

A non-human transgenic mammal containing an exogenous DNA molecule stably integrated in its genome, wherein said exogenous DNA molecule comprises:

(a) 5' regulatory sequences of a mammary gland-specific gene including a promoter;
(b) a Factor IX-encoding DNA sequence that encodes a signal sequence, a Factor IX pro-sequence and a Factor IX sequence in a 5' to 3' direction, wherein said signal sequence is effective in directing the secretion of said Factor IX into the milk of said transgenic mammal and wherein said Factor IX sequence lacks at least a portion of the complete or the complete 5'-untranslated and 3'-untranslated regions of the Factor IX gene.; and
(c) 3' regulatory sequences from a mammary gland-specific gene or 3' regulatory sequences active in a mammary gland;

wherein said 5' and said 3' regulatory sequences are operatively linked to said Factor IX-encoding DNA sequence.

Mammary gland-specific promoters that are useful in the present invention are selected from the group consisting of short whey acidic protein (WAP) promoter, long WAP promoter, short α-casein promoter, short β-casein promoter, short kappa-casein promoter, long α-casein promoter, long β-casein promoter, long kappa-asein promoter, α-lactalbumin promoter and β-lactoglobulin promoter.

Non-human transgenic mammals which are contemplated by the present invention are selected from the group consisting of mice, rats, rabbits, pigs, sheep, goats and cows.

It is a further object to provide a process for producing Factor IX by providing a non-human transgenic mammal having integrated into its genome an exogenous DNA molecule, wherein said exogenous DNA molecule comprises:

(a) providing a non-human transgenic mammal having integrated into its genome an exogenous DNA molecule, wherein said exogenous DNA molecule comprises: (1) 5' regulatory sequences of a mammary gland-specific gene including a promoter; (2) a Factor IX-encoding DNA sequence that encodes a signal sequence, a Factor IX pro-sequence and a Factor IX sequence in a 5' to 3' direction, wherein said signal sequence is effective in directing the secretion of said Factor IX into the milk of said transgenic mammal and wherein said Factor IX sequence lacks at least a portion of the complete or the complete 5'-untranslated and 3'-untranslated regions of the Factor IX gene.; and (3) 3' regulatory sequences from a mammary gland-specific gene or 3' regulatory sequences active in a mammary gland; wherein said 5' and said 3' regulatory sequences are operatively linked to said Factor IX-encoding DNA sequence;
(b) allowing said DNA sequences encoding said Factor IX to be expressed and said Factor IX to be secreted into the milk of said transgenic mammal;
(c) collecting said milk from said mammal; and
(d) isolating said Factor IX from said milk.

It is a further object to provide a method of treating hemophilia B using the Factor IX produced by the transgenic mammal, described above. Treating involves administration of the Factor IX of the invention and a pharmaceutically acceptable carrier to a hemophilia B patient.

It is a further object of the invention to provide an in vitro culture of mammary gland cells that produce Factor IX. Another object of the invention is to provide a method of treating hemophilia B by implanting such Factor IX mammary gland cells into a patient.

BRIEF DESCRIPTION OF THE DRAWINGS

FIG. 1A shows the construction of pWAP4. FIG. 1B shows the production of pUCFIX. FIG. 1C shows the introduction of human FIX cDNA into pWAP4. FIG. 1D shows the production of pUCWAPFIX. FIX cDNA was modified by PCR in order to introduce KpnI sites on the 3' and 5' ends. Using FIX cDNA as a template, PCR primers humFIX5'KpnI and humFIX3'KpnI, as shown in Table 1, below, were used to produce FIX cDNA with KpnI sites on both ends. Modified cDNA may be easily into a "cassette vector" for constructing a chimeric gene.

FIG. 3A shows the production of pUCNotI. FIG. 3B shows the production of of pUCWAP5 and the production of a fragment that contains the pUCNotI vector sequence flanked by mWAP3'UTR. FIG. 3C shows the production of pUCWAP6.

DETAILED DESCRIPTION

1. Overview

Figure 1A:
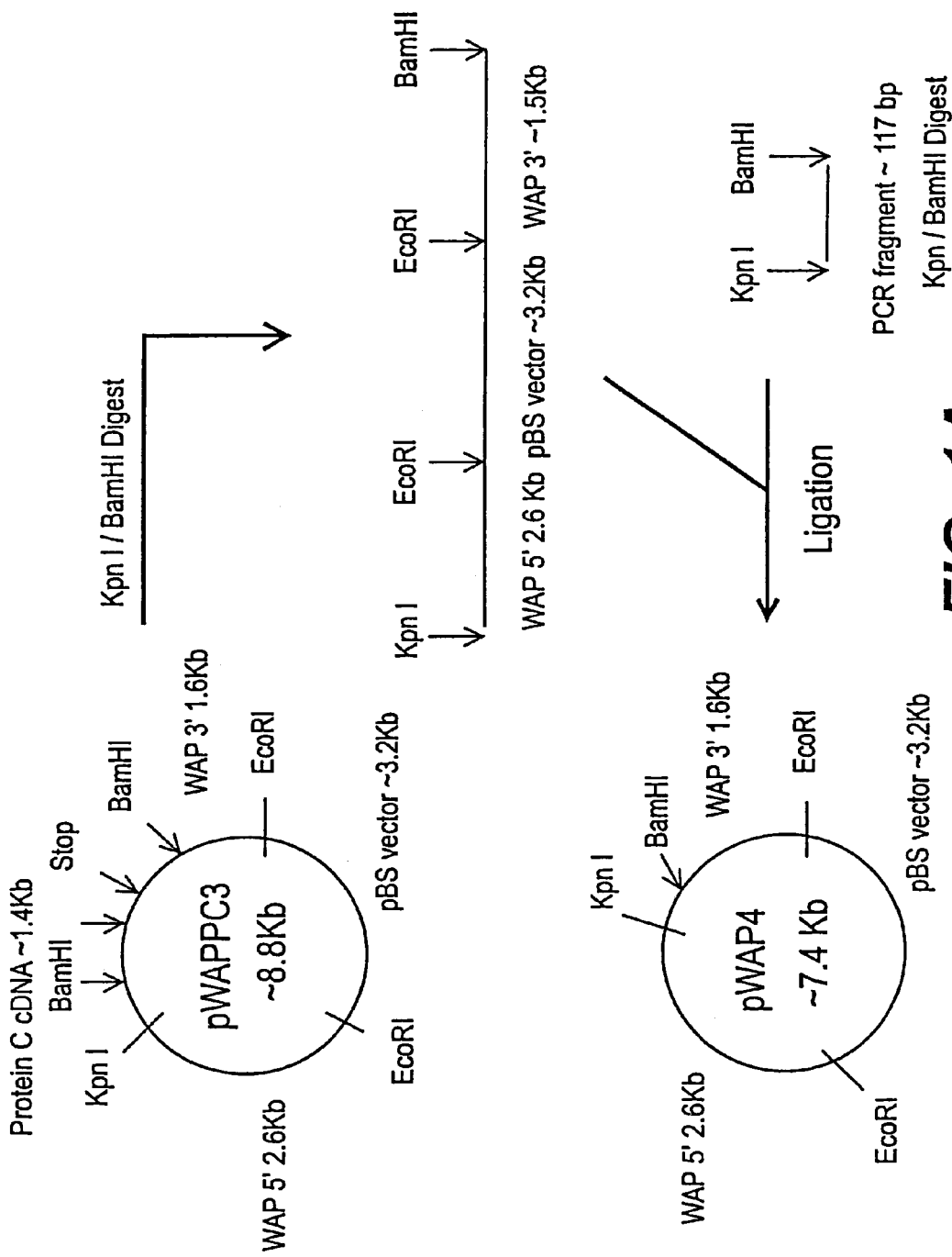
FIGS. 1A-1D schematically depict the construction of a chimeric Factor IX construct. Specifically.

As discussed above, a method for producing significant quantities of Factor IX in transgenic animals has been elusive. Yull et al., *Proc. Nat'l Acad. Sci. USA* 92:10899 (1995), showed that correction of a cryptic RNA splice site increases the amount of Factor IX synthesized by transgenic animals. In these studies, one transgenic mouse line produced about 27 μg of biologically active Factor IX per milliliter of milk, although, Factor IX levels of individual mice of the line varied. Yull et al. speculated that the variation was probably due to epigenetic instability.

In contrast, the studies presented herein show that transgenic pigs can synthesize and secrete high levels (100-200 μg/ml milk) of biologically active recombinant human Factor IX in milk. Based on reduced and nonreduced SDS PAGE, the majority of the recombinant human Factor IX population appears to be a single chain polypeptide having a post-translationally modified structure similar to human Factor IX. The recombinant human Factor IX secreted into pig milk is biologically active and is able to initiate clotting in Factor IX-deficient human plasma. This is the first reported production of high levels of fully active, sufficiently γ-carboxylated, recombinant human Factor IX in the milk of transgenic livestock.

2. Methods for Producing Transgenic Animals

Notwithstanding past failures to express recombinant human Factor IX with suitably high activity in several different expression systems, the present invention provides methods for obtaining recombinant Factor IX characterized by a high percentage of active protein from the milk of transgenic animals. As used herein, the term "animal" denotes all mammalian animals except humans. It also includes an individual animal in all stages of development, including embryonic and fetal stages. A "transgenic" animal is any animal with cells that contain genetic information received, directly or indirectly, by deliberate genetic manipulation at the subcellular level, such as by microinjection or infection with recombinant virus.

The genetic information to be introduced into the animal is preferably foreign to the species of animal to which the recipient belongs (i.e., "heterologous"), but the information may also be foreign only to the particular individual recipient, or genetic information already possessed by the recipient. In the last case, the introduced gene may be differently expressed than is the naturally occurring, or "native," gene.

The language "germ cell line transgenic animal" refers to a transgenic animal in which foreign DNA has been incorporated into a germ line cell, therefore conferring the ability to transfer the information to offspring. If such offspring, in fact, possess some or all of that information, then they, too, are transgenic animals.

The transgenic animals of this invention are other than human, including, but not limited to farm animals (pigs, goats, sheep, cows, horses, rabbits and the like), rodents (such as mice), and domestic pets (for example, cats and dogs). Livestock animals such as pigs, sheep, goats and cows, are particularly preferred.

Preferably, a transgenic animal of the present invention is produced by introducing into single cell embryos appropriate polynucleotides that encode human Factor IX, or fragments or modified products thereof, in a manner such that these polynucleotides are stably integrated into the DNA of germ line cells of the mature animal, and are inherited in normal Mendelian fashion.

In accordance with the invention, DNA molecules can be introduced into embryos by a variety of means to produce transgenic animals. For instance, totipotent or pluripotent stem cells can be transformed by microinjection, calcium phosphate mediated precipitation, liposome fusion, retroviral infection or by other means. The transformed cells can then be introduced into embryos and incorporated therein to form transgenic animals. In a preferred method, developing embryos can be infected with retroviral vectors and transgenic animals can be formed from the infected embryos. In the most preferred method, however, the DNA molecules of the invention are injected into embryos, preferably at the single-cell stage, which are allowed to develop into mature transgenic animals. However, the present invention is not limited to this preferred method but other methods of making transgenic animals can be used as described, for example, in *Transgenic Animal Generation and Use* by L. M. Houdebine, Harwood Academic Press, 1997. Transgenic animals also can be generated using methods of nuclear transfer or cloning using embryonic or adult cell lines as described for example in Campbell et al., *Nature* 380: 64-66 (1996) and Wilmut et al., *Nature* 385: 810-813 (1997). Further a technique utilizing cytoplasmic injection of DNA can be used as described in U.S. Pat. No. 5,523,222.

Factor IX-producing transgenic animals can be obtained by introducing a chimeric construct comprising Factor IX-encoding sequences. An alternative method of producing transgenic animals is to introduce a Factor IX chimeric construct with a second construct that may provide higher expression more frequently than that observed with the use of Factor IX constructs alone. As described herein, such doubly-transgenic, or "bigenic," animals have native WAP genomic sequences that are injected as separate constructs to be concatenated in vivo as additional flanking sequences to the target Factor IX cDNA construct.

Methods for obtaining transgenic animals are well-known. See, for example, Hogan et al., MANIPULATING THE MOUSE EMBRYO, (Cold Spring Harbor Press 1986); Krimpenfort et al., *Bio/Technology* 9:88 (1991); Pallnter et al., *Cell* 41:343 (1985); Kraemer et al., GENETIC MANIPULATION OF THE EARLY MAMMALIAN EMBRYO, (Cold Spring Harbor Laboratory Press 1985); Hammer et al., *Nature* 315:680 (1985); Wagner et al., U.S. Pat. No. 5,175,385; Krimpenfort et al., U.S. Pat. No. 5,175,384, Janne et al., *Ann. Med.* 24:273 (1992), Brem et al., *Chim. Oggi.* 11:21 (1993), Clark et al. U.S. Pat. No. 5,476,995, hereby incorporated by reference.

3. Construction of Chimeric Genes

Suitable Factor IX-encoding DNA used for producing transgenic animals can be obtained using human liver tissue as a source for cloning the human Factor IX gene. The DNA coding for Factor IX can be fused, in proper reading frame, with appropriate regulatory signals, as described in greater detail below, to produce a chimeric construct which is then amplified, for example, by propagation in a bacterial vector, according to conventional practice.

The amplified construct is thereafter excised from the vector and purified for use in microinjection. The purification is preferably accomplished by means of high performance liquid chromatography (HPLC), which removes contamination of the bacterial vector and from polysaccharides typically present when other techniques, such as conventional agarose electroelution, are used: The preferred HPLC method entails sorbing the construct onto an anion-exchange HPLC support and selectively eluting the construct from the support, preferably with an aqueous sodium chloride solution, thereby to eliminate contamination from the vector. Elution also may be effected by other means, such as a pH gradient.

Alternatively, the excised construct can be purified by ultracentrifugation through an aqueous sucrose or sodium chloride gradient, gel electroelution followed by agarose treatment and ethanol precipitation, or low pressure chromatography.

Since it is preferable that the construct have the minimum amount of impurities, more than one cycle of HPLC or other purification is advantageous. In particular, the use of HPLC-purified DNA for microinjection, as described above, allows for remarkably high transformation frequencies, on the order of 20% or more, for example, in mice and pigs.

DNA constructs useful in the present invention provide a DNA sequence encoding Factor IX, preferably human Fact6r IX, operably linked to all the cis-acting signals necessary for mammary tissue specific expression of Factor IX, post-translational modification of Factor IX, secretion of Factor IX into milk, and full biological activity of Factor IX. Although the present invention preferably entails the use of DNA constructs that produce the desired or native human Factor IX per se, the desired protein also may be produced as a fusion protein containing another protein. For example, the desired recombinant protein of this invention may be produced as part of a larger recombinant protein in order to stabilize the desired protein or to make its purification from milk faster and easier. The fusion partners then are separated chemically or enzymatically, and the desired protein isolated.

Methods for obtaining human-Factor IX-encoding DNA molecules and nucleotide sequences of human Factor IX gene and cDNA are provided, for example, by Kurachi et al., *Proc. Nat'l Acad. Sci. USA* 79:6461 (1982), Choo et al., *Nature* 299:178 (1982), Anson et al., *EMBO J.* 3:1053 (1984), Brownlee et al., international publication No. WO 84/00560, Yull et al., *Proc. Nat'l Acad. Sci. USA* 92: 10899 (1995), Clark, international publication No. WO 95/30000, and Meulien, U.S. Pat. No. 5,521,070 (1996). Human Factor IX probes also can be obtained from the American Type Culture Collection, Rockville, Md. (e.g., ATCC Nos. 61385, 79588, 79602, or 79610).

Alternatively, Factor IX-encoding DNA molecules may be obtained by synthesizing the genes with mutually priming long oligonucleotides. See, for example, Ausubel et al., supra, at pages 8.2.8 to 8.2.13; Wosnick et al., *Gene* 60:115 (1987). Moreover, the polymerase chain reaction can be used to synthesize DNA fragments as large as 1.8 kilobases in length. Bambot et al., *PCR Methods and Applications* 2:266 (1993).

Suitable Factor IX-encoding DNA molecules include genomic or complementary DNA molecules that encode naturally occurring Factor IX. In a preferred embodiment, DNA molecules encoding human Factor IX are employed, including cDNA and genomic DNA molecules. However, the present invention discloses that a cDNA based construct as described herein can be successfully used for the expression of human Factor IX at commercially useful levels. Particularly, a cDNA based construct containing 5' regulatory sequences of a mammary gland specific gene including a promoter, a Factor IX-encoding DNA sequence as described herein, and 3' regulatory sequences from a mammary gland-specific gene or 3' regulatory sequences active in a mammary gland is preferred. Factor IX-encoding DNA molecules from other species may also be used, such as the Factor IX encoded by rats, pigs, sheep, cows and chimpanzees.

It also will be appreciated that the Factor IX cDNA fragment described herein can be modified using recombinant DNA techniques to obtain functionally equivalent molecules. For example, 3' or 5' portions of the Factor IX gene can be added, or completely deleted, or a few bases at either end may be removed. Introns can be removed or added, or portions of one or more introns can be deleted. Additional nucleotide sequences can be inserted into them. The sequences of the introns can be altered. Exons can be modified in accordance with the discussion of modified Factor IX molecules set forth below. Most modified forms of the preferred Factor IX cDNA fragment will not be significantly changed in their ability in transgenic animals to engender the production of milk-born Factor IX. In one embodiment, the Factor IX encoding portion of the gene lacks the complete 5'-untranslated and 3'-untranslated regions of the native Factor DX gene. Thus, these substantially similar fragments will be equivalent in the invention to the particularly disclosed Factor IX cDNA fragment.

A 5'-untranslated region that is not the 5'-untranslated region of the Factor IX gene can be included in the present DNA Factor IX constructs, particularly the 5'-untranslated region of the mouse WAP gene. Likewise a 3'-untranslated region that is not the 3'-untranslated region of the Factor IX gene, particularly the 3'-untranslated region of the mouse WAP gene.

Further, the Factor IX-encoding DNA molecule can also comprise a 5'-untranslated region located 5' from the signal sequence DNA, and a 3'-untranslated region located 3' from the Factor IX coding sequence.

Additional useful modifications of Factor IX include those that alter post-translational modifications, size or active site, or that fuse this protein or portions thereof to another protein. Such modifications can be introduced into the protein by techniques well known in this art, such as, by synthesizing modified genes by ligation of overlapping oligonucleotide or introducing mutations into the cloned genes by, for example, oligonucleotide-mediated mutagenesis. See, generally, Ausubel et al. (eds.), CURRENT PROTOCOLS IN MOLECULAR BIOLOGY, pages 8.0.3-8.5.9 (1990); McPherson (ed.), DIRECTED MUTAGENESIS: A PRACTICAL APPROACH, IRL Press (1991).

The examples described herein demonstrate that a transgenic animal can be produced that synthesizes a sufficiently γ-carboxylated, biologically active Factor IX in mammary tissue. Accordingly, the basic methods of the present application can be used to obtain transgenic animals that produce other vitamin K-dependent blood coagulation factors, such as Factor II, Factor VII, Factor X, or the anticoagulation protein, Protein S. DNA molecules encoding these proteins can be obtained by standard methods. See, for example, Pollak et al., *J. Biol. Chem.* 271: 1738 (1996), which describes the characterization of the Factor VII gene, which is located on chromosome 13 just 2.8 kilobase pairs 5' to the Factor X gene.

The cis-acting regulatory regions useful in the invention include the promoter that drives expression of the Factor IX gene. Promoters particularly useful in the invention are "active" in mammary tissue in that the promoters are more active in mammary tissue than in other tissues under physiological conditions where milk is synthesized. Most preferred are promoters that are both specific to and efficient in mammary tissue. By "efficient" it is meant that the promoters are strong promoters in mammary tissue that can support the synthesis of large amounts of protein for secretion into milk. Among such promoters, highly preferred are the short and long whey acidic protein (WAP), short and long α, β and kappa casein, α-lactalbumin and β-lactoglobulin ("BLG") promoters.

Promoters may be selected on the basis of the protein compositions of milk from various species. For example, the WAP and BLG promoters are particularly useful with transgenic rodents, pigs and sheep. The rodent WAP short and long promoters have been used to express the rat WAP gene, the human tissue-type plasminogen activator gene and the CD4 gene, while the sheep BLG promoter has been used to express the sheep BLG gene, the human alpha-1-antitrypsin gene and the human Factor IX gene. See, for example, Paleyanda et al., 1991, above, and Clark et al., *TIBTECH* 5: 20 (1987). Preferred promoters include the rodent casein and WAP promoters, and the casein, α-lactalbumin and BLG promoters from porcine, bovine, equine and ovine (pigs, sheep, goats, cows, horses), rabbits, rodents and domestic pets (dogs and cats). The genes for these promoters have been isolated and their nucleotide sequences have been published. See, for example, Clark et al. (1987), above, and Henninghausen, *Protein Expression and Purification* 41: 3 (1990).

A useful promoter may be isolated by carrying out conventional restriction endonuclease and subcloning steps. A mouse WAP promoter, isolated as a 2.6 kb EcoRI-KpnI fragment immediately 5' to the WAP signal sequence, is preferred, although the "long" WAP promoter (the 5' 4:2 kb Sau3A-KpnI promoter of the mouse WAP gene, or a fragment thereof) is also suitable for carrying out this invention. The publication of Paleyanda et al., *Transgenic Research* 3: 335 (1994), for example, provides examples of a suitable short mouse WAP promoter ("2.5 kb mWAP promoter") and a long mouse WAP promoter ("4.1 kb mWAP promoter"). Pages 336-339 of the Paleyanda publication are incorporated by reference. Also see, for example, Gordon et al., *Bio/Technology* 5: 1183 (1987); McKnight et al., "The Whey Acidic Protein," in GENES, ONCOGENES, AND HORMONES: ADVANCES IN CELLULAR AND MOLECULAR BIOLOGY OF BREAST CANCER, Dickson et al. (eds.), pages 399-412 (Kluwer Academic Publishers 1991). Additional regulatory sequences direct secretion of proteins into milk and/or other body fluids of the transgenic animal. In this regard, both homologous and heterologous regulatory sequences are useful in the invention. Generally, regulatory sequences known to direct the secretion of milk proteins, such as either signal peptides from milk or the nascent target polypeptide, can be used, although signal sequences can also be used in accordance with this invention that direct the secretion of expressed proteins into other body fluids, particularly-blood and urine. Examples of such sequences include the signal peptides of secreted coagulation factors including signal peptides of Factor IX, protein C, and tissue-type plasminogen activator.

Among the useful sequences that regulate transcription, in addition to the promoters discussed above, are enhancers, splice signals, transcription termination signals, polyadenylation sites, buffering sequences, RNA processing sequences and other sequences which regulate the expression of transgenes. Particularly useful in this regard are those sequences that increase the efficiency of the transcription of the genes for Factor IX in the mammary gland or other cells of the transgenic animals listed above. Preferred are transcription regulatory sequences for proteins highly expressed in the mammary gland cells.

Preferably, the expression system or construct of this invention also includes a 3' untranslated region downstream of the DNA sequence encoding the desired recombinant protein, or the 3' untranslated region of the milk protein gene or the milk protein gene with its 3' untranslated region, any of which can be used for regulation. This region can increase expression of the transgene. This region apparently stabilizes the RNA transcript of the expression system and thus increases the yield of the desired protein. Among the 3' untranslated regions useful in this regard are sequences that provide a poly A signal.

For expression of Factor IX, it is preferred that the 3' untranslated region is not obtained from the native human Factor IX gene. Suitable heterologous 3'-untranslated sequences can be derived, for example, from the SV40 small t antigen, the casein 3' untranslated region, or other 3' untranslated sequences well known in this art. Preferably, the 3' untranslated region is derived from a milk-specific protein, such as the WAP protein. The stabilizing effect of this region's poly A transcript is important in stabilizing the mRNA of the expression sequence. Ribosome binding sites are also important in increasing the efficiency of expression of Factor IX. Likewise, sequences that regulate the post-translational modification of Factor IX are useful in the invention.

In a particularly preferred embodiment, the transgenes of the invention generally consist of WAP milk protein regulatory sequences upstream and downstream flanking the Factor IX cDNA/signal peptide sequences. A native 5'-WAP regulatory sequence ending in an accessible restriction site immediately before/at the ATG codon may be ligated to the restriction sites that occur at the ATG of translatable sequences with no linker sequences derived from the chains of human Factor IX. Each of the combined 5'-regulatory and Factor IX translatable sequences ending in a particular restriction site may then be ligated to a corresponding restriction site which occurs at the beginning of the 3'-untranslated region of WAP and adjoining WAP 3'-flanking region. This construction motif enables native 5'-regulatory and 3'-untranslated region of the milk protein genes to be immediately juxtaposed without intervening sequences. Particular restriction sites at the ends of all constructs may be selected in order to facilitate concatenation of constructs into a single domain within the animal genome.

Thus, in accordance with the present invention a DNA molecule that encodes Factor IX is operably linked to cis-acting regulatory sequences which allow for efficient expression of Factor IX in milk. The resulting chimeric DNA is introduced into a mammalian embryo, where it integrates into the embryonic genome and becomes part of the heritable genetic endowment of all the cells, including the germ line cells, of the adult which develops from the embryo. The Factor IX which is expressed in the mammary tissue and secreted into the milk of a transgenic mammal obtained in this manner displays a surprisingly high percentage of active protein, as measured by enzymatic and coagulation-inhibition assays which are conventionally employed to detect Factor IX activity, such as ELISAs, chromogenic activity assays and coagulation inhibition assays.

4. Isolation of Factor IX from the Milk of Transgenic Animals

Obtaining milk from a transgenic animal according to the present invention is accomplished by conventional means. See, for example, McBurney et al., *J. Lab. Clin. Med.* 64:485 (1964); Velander et al., *Proc Nat'l Acad. Sci. USA* 89:12003 (1992). Factor IX, or fragments thereof, can be isolated and purified from milk or urine by conventional means without deleteriously affecting activity. A preferred method of isolation from milk consists of a combination of anion exchange and immunochromatography, cryoprecipitations, zinc ion-induced precipitation of either whole milk or milk whey (defatted milk) proteins. See, for example, Bringe et al., *J. Dairy Res.* 56:543 (1989).

Milk is known to contain a number of proteases that have the potential to degrade foreign proteins. These include an alkaline protease with tryptic and chymotryptic activities, a serine protease, a chymotrypsin-like enzyme, an aminopeptidase and an acid protease. Clark et al. (1987) above. It may be desirable, therefore, to protect newly secreted Factor IX, or fragments thereof, against proteolytic degradation. Such precautions include rapid processing of the milk after collection and addition to the milk of well known inhibitors of proteolysis, such as are listed in SIGMA CHEMICAL CO. CATALOG (1993 edition) at page 850.

Thus, in one embodiment, the transgenic mammal of the present invention produces active human Factor IX. For instance, in one embodiment wherein said mammal is a pig, such pig secretes from about 100 to about 220 μg of active human Factor IX per milliliter milk. In another embodiment, such pig secretes from abort 100 to about 185 μg of active human Factor IX per milliliter milk, from about 100 to about 170 μg of active human Factor IX per milliliter of milk, from about 135 to about 220 μg of active human Factor IX per milliliter of milk or from about 145 to about 220 μg of active human Factor IX per milliliter of milk, as set forth below.

Factor IX produced from the transgenic mammal according to the invention has a specific activity which is at least about 5 to 200 percent greater than the specific activity of human Factor IX isolated from human plasma, as determined by an activated partial thromboplastin clotting time assay. In another embodiment, the specific activity of Factor IX produced by the transgenic mammal of the invention is at least about 10 to 100 percent greater, at least about 15 to 50 percent greater or at least about 15 to about 46 percent greater than the specific activity of human Factor IX isolated from human plasma.

In another embodiment, the invention relates to an in vitro culture of mammary gland cells explanted from the transgenic mammal of the invention. Such cells are explanted and cultured in vitro, according to methods well known to the skilled artisan. See e.g., U.S. Pat. No. 5,580,781. In another embodiment, Factor IX is isolated and purified from the in vitro cell culture, according to methods well known to the skilled artisan.

5. Treatment Methods

In another embodiment, the present invention relates to a method of treating hemophilia B using Factor IX produced by the transgenic mammal of the invention. Specifically, treatment includes the prevention or amelioration of the symptoms of hemophilia B in hemophilia B patients. Symptoms of hemophilia B include excessive bleeding upon injury, spontaneous bleeding, especially into weight-bearing joints, soft tissues and mucous membranes. Repeated bleeding into joints results in hemarthroses, which causes painful crippling arthropathy that necessitates joint replacement. Hematomas in-soft tissues may result in "pseudo" tumors composed of necrotic coagulated blood. Such blood can obstruct, compress or rupture into adjacent organs and can lead to infection. Bleeding into gastrointestinal tract, central nervous system, intracranium or airway/retroperitoneal space can lead to death if not detected. This, treatment according to the present invention includes the prevention or amelioration of bleeding and the related side effects found in hemophilia B patients. This method involves administering to a patient having hemophilia B symptom, a hemophilia B symptom preventing or ameliorating amount of Factor IX produced by the transgenic mammal of the present invention. Administration may be accomplished by any method known to the skilled artisan. For instance, the treatment of the above described symptoms may consist of intravenous replacement therapy with Factor IX concentrates. Treatment of major bleeding episodes may be by bolus injection of concentrate. However, as described above, tissue damage may remain even after prompt detection and treatment. Prophylactic treatment is recommended to prevent pain and debilitation. Upon injection, 50% of Factor IX, according to the invention, is immediately bound to vascular endothelial cells and/or diffuses into the extravascular space. The remaining 50% has a half life in circulation of approximately 24 hours. These infusion kinetics result in the need for injections about once to twice per week to maintain minimal therapeutic levels in the plasma.

Another embodiment of the invention relates to pharmaceutical compositions comprising the Factor IX of the present invention. Such pharmaceutical composition preferably is Factor IX produced by the above described transgenic animal and a pharmaceutically acceptable carrier. For instance, such pharmaceutical composition may be a stable liquid formulation of the Factor IX of the invention that can be administered by continuous infusion to provide a constant circulating level of the coagulation factor.

The Factor IX produced by the transgenic animal of the present invention may be concentrated and sold in lyophilized form, according to methods well known to the skilled artisan. For instance, the Factor IX of the present invention which has been lyophilized may be reconstituted with sterile water for injection (WH) and delivered in a composition of: 0.01 moles/liter histidine, pH 7.05; 0.066 moles/liter sodium chloride; 3% mannitol. In another embodiment, lyophilized Factor IX is reconstituted in sterile WFI and delivered in a composition that includes: 0.04 units heparin/unit FIX; 1 milligram dextrose/unit Factor IX. To avoid repeated invasive treatments as is found with the current therapies for prophylaxis, stabilities of at least 30 days at 37° C. and at least 365 days at 4° C. are preferred. The present invention provides significant stability over that of these preparations reconstituted.

This skilled artisan would know of other suitable formulations for the Factor IX of the present invention:. See, for instance, Alp haNine by Therapeutic Corporation, Los Angeles, Calif., and Bebulin V H, by Immuno, Vienna, Austria. Of course, any formulations according to the present invention are highly purified and free of viruses, prions, blood-group antibodies, immune complexes and phospholipids.

Dosages or amounts that prevent or ameliorate the symptoms of hemophilia B are necessarily dictated by the clinical picture and severity of the disease. Because there is so much variability between patients and their clinical conditions, monitoring of coagulation function is essential in during any therapy using the Factor IX of the invention. As a rule, on initial treatment, one unit of Factor IX per kg body weight gives a mean rise in Factor IX activity of about 0.5-1%, on continuation therapy, the mean rise is about 1-1.5% Examples of dosages for long term prophylaxis of symptoms of hemophilia B are about 18-30 IU/kg (1× weekly) or about 9-15 IU/kg (2× weekly). Dosages also will vary depending upon the purpose of the treatment. For instance, where a hemophilia B patient has had surgery, it may be desirable to raise Factor IX levels in such patients by 30 to 50% following the week of surgery. For dental extractions, the Factor IX levels may need to be raised to 50% immediately prior to the surgery. Mild to moderate hemorrhages may be treated with a single administration of the Factor IX of the invention to raise Factor IX levels to 20 to 30%. In the even to more serious hemorrhages, it may be desirable to raise Factor IX levels to 30 to 50% and infusions may be required daily. Again, those of skill in the art would know how to adjust the amount and frequency of dosages of the Factor IX of the present invention depending upon the patient and the clinical setting.

In yet another embodiment, the invention relates to a method of treating hemophilia B using Factor IX-producing cells that are explanted from the transgenic mammal of the present invention. Such mammary gland cells express Factor IX in vivo, thereby preventing or ameliorating the symptoms of hemophilia B. This method is accomplished by using known techniques for gene therapy. See e.g., Debs, R. *Proc. Natl' Acad. Sci.* (*USA*) 89: 11277-11281 (1992), Legendre et al., *Pharmaceutical Res.* 9: 1235-42 (1992). In one embodiment, Factor IX-producing cells removed from the transgenic mammal according to the invention are cultured in an in vitro culture system prior to transplantation into a human. Such culture systems are well known to the skilled artisan. See e.g. U.S. Pat. No. 5,580,781. The cells are treated and then transplanted into the patient in a manner so as to avoid rejection by the recipient. Such methods are known to the skilled artisan. See, for instance, U.S. Pat. No. 5,573,934, which teaches a method of encapsulating biological material for use in vivo. Other techniques known to the skilled artisan involve placing the biological material in a chamber of an immunoisolation apparatus and for enhancing the vascular support for the implanted material using immunomodulatory agents. See, U.S. Pat. No. 5,569,462.

The present invention, thus generally described, will be understood more readily by reference to the following examples, which are provided by way of illustration and are not intended to be limiting of the present invention.

EXAMPLE 1

Preparation of a Human Factor IX Expression Vector for Production of Transgenic Pigs Generally, the entire murine WAP gene including 2.5 kb of 5' untranslated sequence and 3' untranslated regions was cloned by standard methods. See Campbell et al., *Nucleic Acids Res.* 12:8685 (1984). A cDNA fragment encoding human Factor IX was obtained and the 3' untranslated region was deleted. Using standard methods, an expression vector was constructed that contained a mouse WAP promoter, isolated as a 2.6 kb EcoRI-KpnI fragment immediately 5' to the WAP signal sequence, the human Factor IX cDNA sequence lacking a 3' untranslated region, and a 1.6 kb fragment of the 3' untranslated region of the WAP gene. A second expression vector contained a 7.2 kb mouse WAP gene (EcoRI-EcoRI) fragment. Expression vectors were amplified by bacterial transformation and purified from bacterial cultures using standard methods. Routine recombinant DNA techniques can be found, for example, in Sambrook et al., MOLECULAR CLONING, A LABORATORY MANUAL, Vol. 1-3 (Cold Spring Harbor Press 1989).

More specifically, a chimeric Factor IX construct was prepared, as follows:

1. Preparation of a Chimeric Factor IX Construct Production of pWAP4 "Cassette Vector"

Regulatory 5' and 3' flanking sequences of the mouse WAP gene were used for mammary specific expression. Specifically, a cassette vector containing a mouse WAP promoter, defined as a 2.6. kb EcoRI-KpnI fragment immediately 5' to the WAP signal sequence and a 1.5 kb fragment of the 3' untranslated region of the WAP gene was prepared. These regulatory sequences do not include coding and intragenic untranslated sequences (introns) of the WAP gene.

The vector designated pWAP4 was derived from pWAPPC3 (C. Russell, dissertation "Improvement of Expression of Recombinant Human Protein C in the Milk of Transgenic Mammal Using a Novel Transgenic Construct," Virginia Technology Institute, Blacksburg, Va. (December 1993)) and was developed as follows: Using WAPPC3 as a template, PCR primers WAP3'S2 (which contains a 5'KpnI site and is homologous to endogenous WAP right after the stop signal) and WAP3'A1, as shown in Table 1, below, were used to produce a segment with KpnI and BamHI sites on either end. This segment was digested with KpnI/BamHI and ligated with the vector containing the fragment from KpnI\BamHI digested pWAPPC3. The ligation mixture was used to transform $E.$ $coli$ DH5α cells by electroporation with resultant colonies grown on LB ampicillin plates. Picked colonies were grown up in TB ampicillin broth, plasmids isolated and cut with Kp4l, BamHI or both and subjected to gel electrophoresis. Sequencing was performed using WAP3'A1 primer and judged as being correct. See FIG. 1A.

Production of Modified (Kpn I) FIX cDNA

The FIX cDNA (containing Kpn I sites located immediately before the start sequence and after the stop sequence) was generated as a PCR fragment. Fragment production protocol is as follows: 100 μl total volume containing 200 μM dNTP's, 0.5 μM of each primer (humFIX5'KpnI and humFIX3'KpnI, as shown in Table 1), 2.5 units Pfu polymerase and 30 ng of plasmid template (pMCDSFIX obtained from Prof. Darryl Stafford, Department of Biology, University of North Carolina, Chapel Hill, N.C., USA), reaction mixture was subjected to 30 cycles of denaturation at 95° C. for 20 sec, annealing at 50° C. for 1 min and elongation at 75° C. for 5 min 45 sec. After cycling, the reaction mixture was subjected to blunting with T4 DNA polymerase for 10 min, EDTA concentration brought up to 25 mM, heated to 65° C. for 15 min, and extracted with Phenol: Chloroform (1:1), precipitated with equal volumes of 95% ethanol, aspirated, and suspended in $H_2O$.

Ligation, Transformation and Sequencing

Figure 1B:
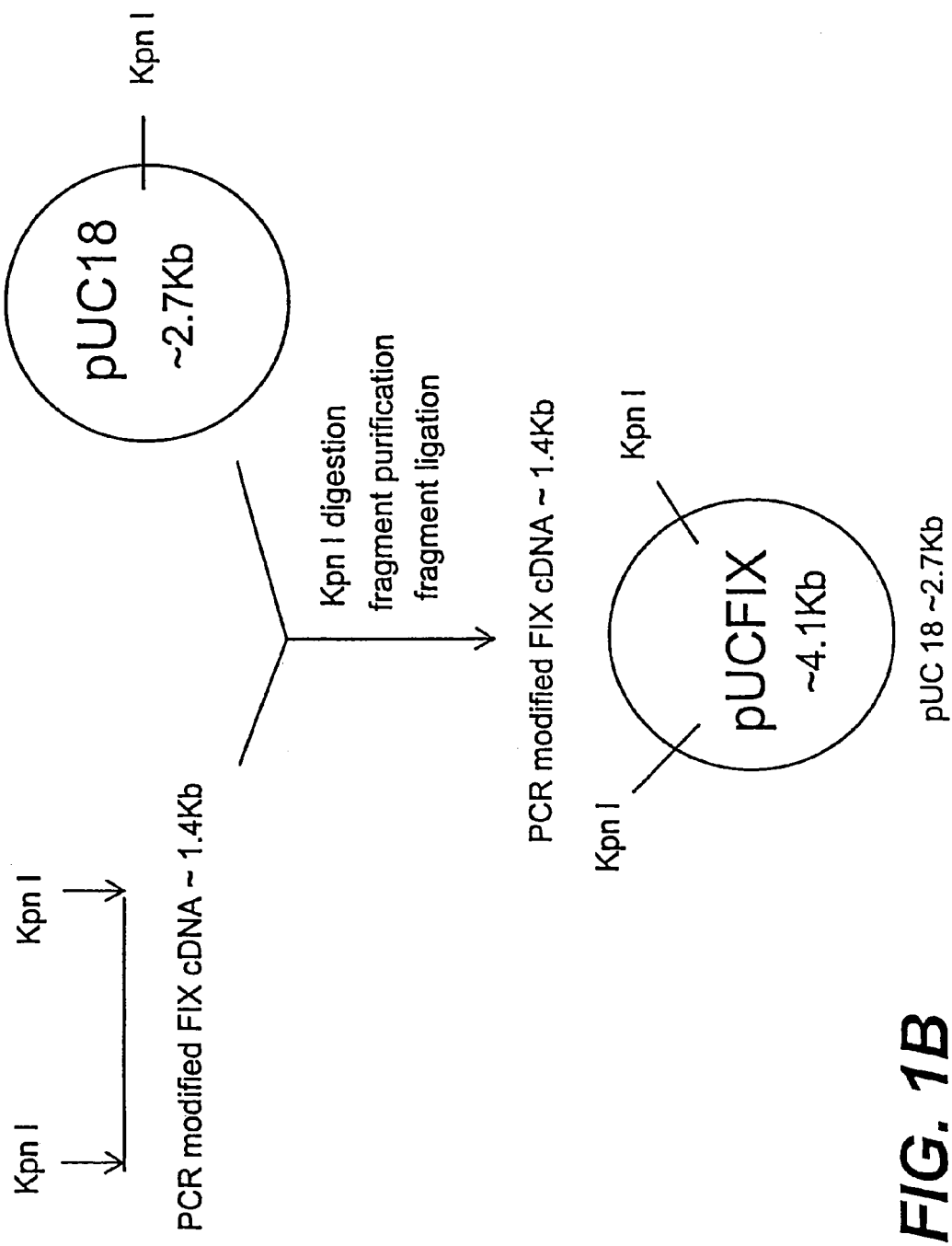

As is shown in FIG. 1B, the plasmid designated pUCFIX containing the modified (Kpn I ends) FIX cDNA was produced by digestion of both pUC18 and the modified cDNA with Kpn I (per manufacturers instructions, Stratagene, La Jolla, Calif.) purification of digestion products by $CHCl_3$: Phenol (1:1) extraction, precipitation with equal volumes of 95% ethanol, aspiration and suspension in $H_2O$. Ligation of plasmid and cDNA was per manufacturers instructions (Stratagene) using 125 ng of Kpn I digested pUC18 and 125 ng of Kpn I digested modified cDNA. $E.$ $coli$ JM109 was transformed by electroportation using ligation mixture and plated on LB ampicillin plates. Selected colonies were grown up in TB ampicillin broth. Plasmid preparations from these colonies were analyzed by restriction enzyme digestion (Kpn I) and gel electrophoresis. The entire sense strand of the cDNA was sequenced and found to be correct as compared with FIXA sequences located in Genebank.

Introduction of FIX cDNA into pWAP4 "Cassette Vector" to Produce pWAPFIX

Figure 1C:
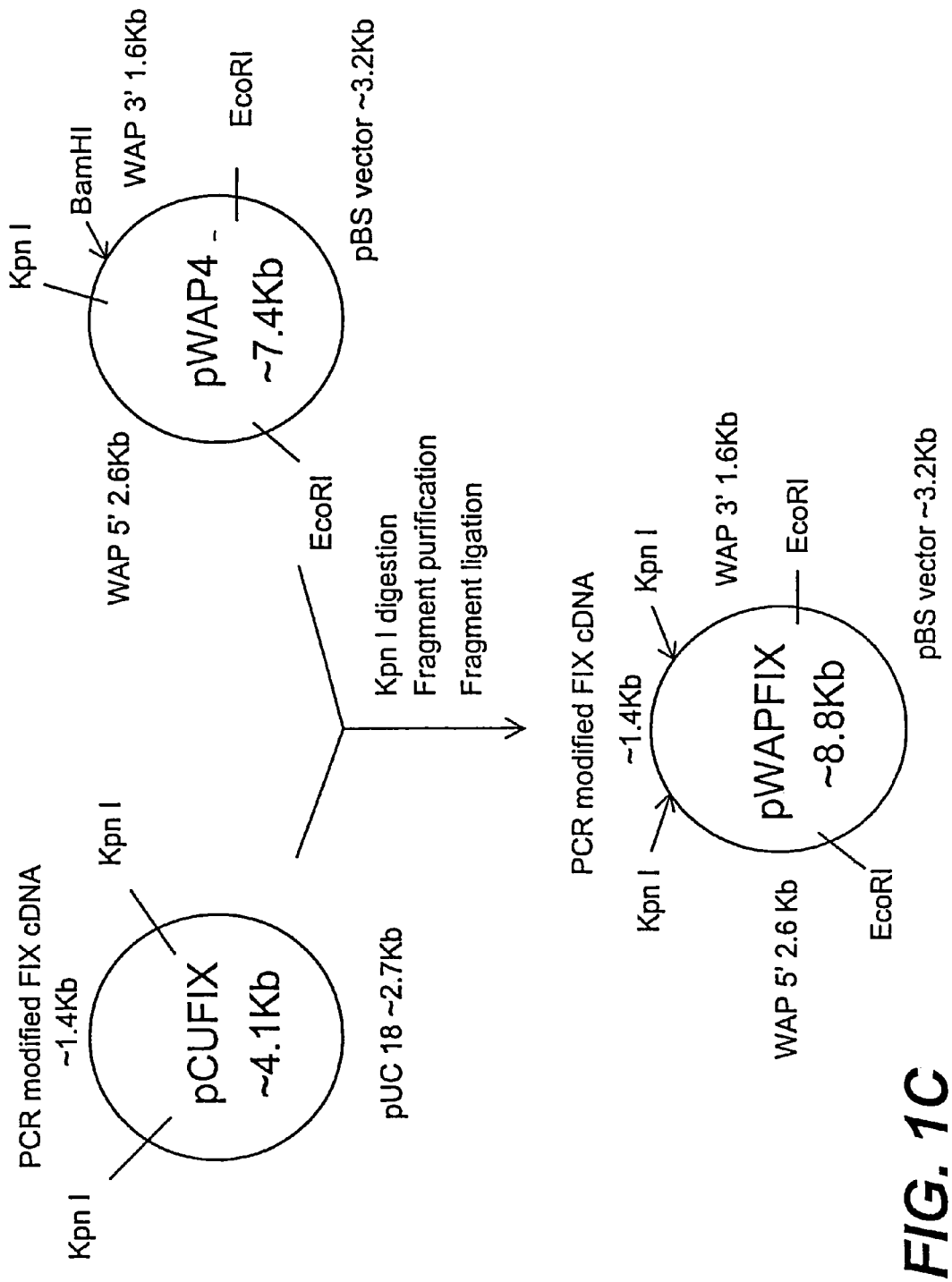

As shown in FIG. 1C, both pWAP4 and pUCFIX were digested with Kpn I in separate reactions, subjected to gel electrophoresis and the appropriate plasmid fragments removed from the gel and ligated. $E.$ $coli$ JM109 was transformed by electroportation using ligation mixture and plated on LB ampicillin plates. Selected colonies were grown up in TB ampicillin broth. Plasmid preparations from these colonies were analyzed by restriction enzyme digestion (Kpn I) then gel electrophoresis. Clones positive for the insert were subjected to PCR analysis using primers FIXS1 and WAP3'A1 to determine the correct orientation of the insert.

Production of pUCWAPFIX

Figure 1D:
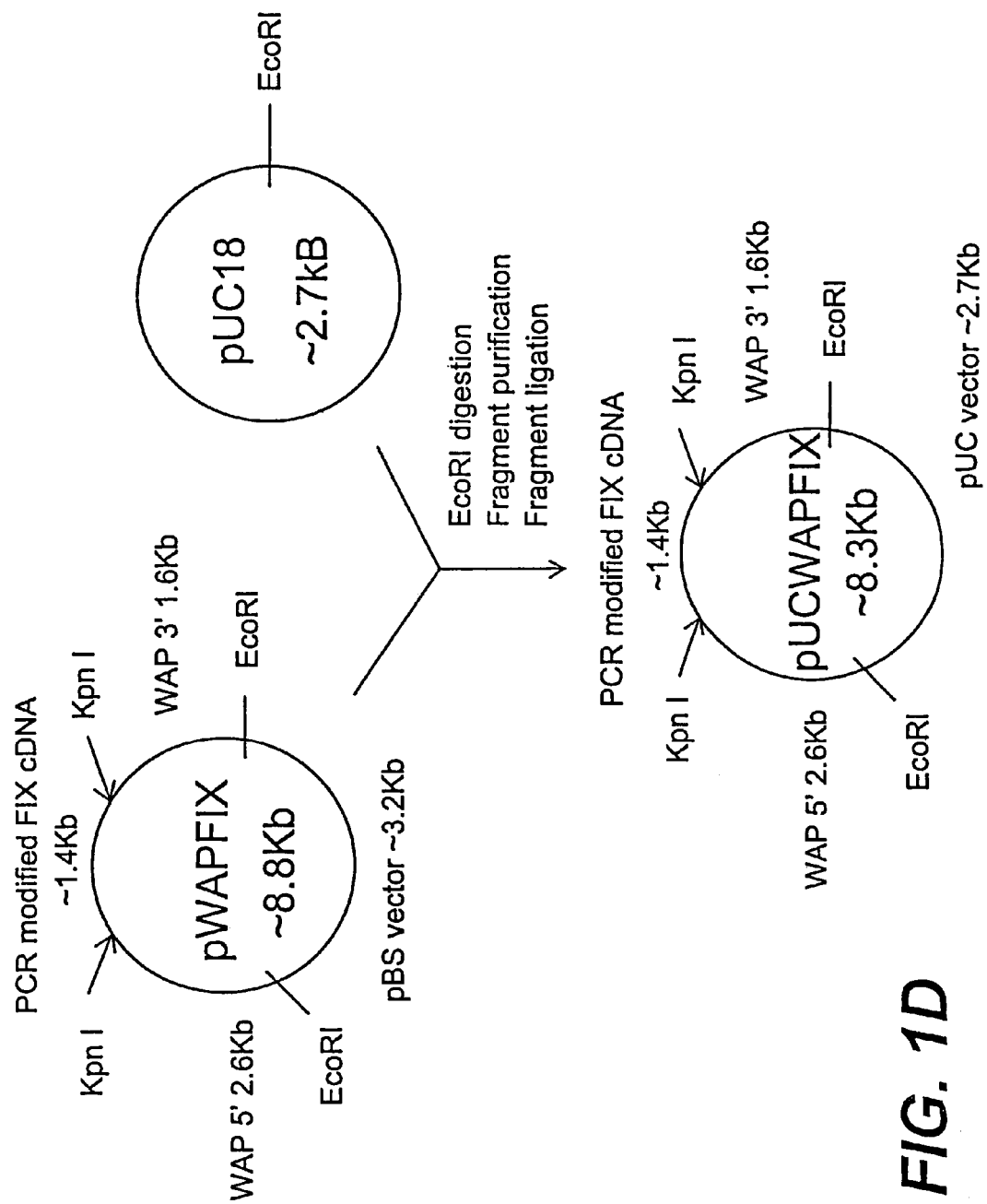

As shown in FIG. 1D, the insert containing WAP promoter, cDNA and 3'WAP UTR was released from pWAPFIX by EcoR I digestion, subjected to gel electrophoresis, removed from the gel and purified. This fragment was ligated with Kpn I digested pUC18 and the reaction mixture used to transform $E.$ $coli$ JM109 by electroportation. After electroportation, cells were plated on LB ampicillin plates with picked colonies grown in TB ampicillin broth. Plasmids from picked colonies were purified and subjected to EcoRI enzyme digestion and electrophoresis. After insert confirmation, large scale purification was undertaken, according to methods well known to the skilled artisan.

2. Preparation of Factor IX-Encoding DNA for Microinjection

Chimeric constructs containing either the 7.2 kb mouse WAP gene, or containing the WAP promoter, human Factor IX gene and 3' WAP sequence were excised from pUCWAP-FIX by EcoRI restriction digest and purified for microinjection using low melting point agarose electrophoresis. The DNA: agarose band was cut from the gel slab. The agarose band was then treated with agarase to degrade and remove agarose contamination.

After digestion, the solution containing the cDNA was brought to 10 mM Mg2+, 20 mM EDTA and 0.1% SDS and then extracted with phenol/chloroform. DNA was precipitated from the aqueous layer with 2.5 volumes of ethanol in the presence of 0.3 M sodium acetate ate –20 degrees centigrade overnight. After centrifugation, the pellet was washed with 70% ethanol, dried, and each of the constructs was resuspended and dissolved in Brinsters microinjection buffer to a concentration of 1.4 or 7 μg/ml (for mice), 14 μg/ml (for pigs).

According to another protocol, extracted DNA was purified by HPLC, as follows. After cleaving a chimeric gene from its vector, the solution was brought to 10 mM magnesium, 20 mM EDTA and 0.1% SDS and then extracted with phenol/chloroform. DNA was precipitated from the aqueous layer with 2.5 volumes of ethanol in the presence of 0.3 M sodium acetate at −20° C. overnight. After centrifugation, the pellet was washed with 70% ethanol, dried, and resuspended in sterile distilled water.

The digested DNA was precipitated with isopropanol and then dissolved in TE buffer at 0.3 μg/ml. Fragments were purified by HPLC using a Waters GEN FAX PAC HPLC column. The column was run isocratically using a buffer consisting of 25 mM Tris-HCl (pH 7.5), 1 mM sodium EDTA, and 0.63 M NaCl. About 15 μg of digested DNA was loaded on the column at a time. DNA samples from all of the chromatographic runs were then pooled, reprecipitated, and run through the column a second time.

DNA concentrations were determined by agarose gel electrophoresis by staining with ethidium bromide and comparing the fluorescent intensity of an aliquot of the DNA with the intensity of standards. Samples were then adjusted to 10 μg/ml and stored at −20° C., prior to microinjection.

EXAMPLE 2

Production of Transgenic Pigs that Express the Human Factor IX Gene

Pig embryos were recovered from the oviduct, and were placed into a 1.5 ml microfuge tube containing approximately 0.5 ml embryo transfer media (Beltsville Embryo Culture Medium). Embryos were centrifuged for 12 minutes at 16,000×g RCF (13,450 RPM) in a microcentrifuge (Hermle, model Z231). The embryos were then removed from the microfuge tube with a drawn and polished Pasteur pipette and placed into a 35 mm petri dish for examination. If the cytoplasm was still opaque with lipid such that pronuclei were not visible, the embryos were centrifuged again for 15 minutes. Embryos were then placed into a microdrop of media (approximately 100 μl) in the center of the lid of a 100 mm petri dish, and silicone oil was used to cover the microdrop and fill the lid to prevent media from evaporating. The petri dish lid containing the embryos was set onto an inverted microscope (Carl Zeiss) equipped with both a heated stage and Hoffman Modulation Contrast optics (200× final magnification). A finely drawn (Kopf Vertical Pipette Puller, model 720) and polished (Narishige microforge, model MF-35) micropipette was used to stabilize the embryos while about 1-2 picoliters of HPLC-purified DNA solution containing approximately 200-500 copies of a mixture of the two chimeric constructs was delivered into the male pronucleus with another finely drawn micropipette. Embryos surviving the microinjection process as judged by morphological observation were loaded into a polypropylene tube (2 mm ID) for transfer into the recipient pig.

EXAMPLE 3

Production of pUCWAP6 "Cassette Vector" and Plasmid pUCWAP6FIX Production of pUCWAP6 "Cassette Vector"

Generally, the entire murine WAP gene was cloned by standard methods, as described above in Example 1, and regulatory 5' and 3' flanking sequences of the mouse WAP gene were used for mammary specific expression. Specifically, a cassette vector containing a mouse WAP promoter, defined as a 4.1 kb NotI-KpnI fragment immediately 5' to the WAP signal sequence and a 1.6 kb fragment of the 3' untranslated region of the WAP gene was prepared. These regulatory sequences do not include coding and intragenic untranslated sequences (introns) of the WAP gene.

Figure 3A:
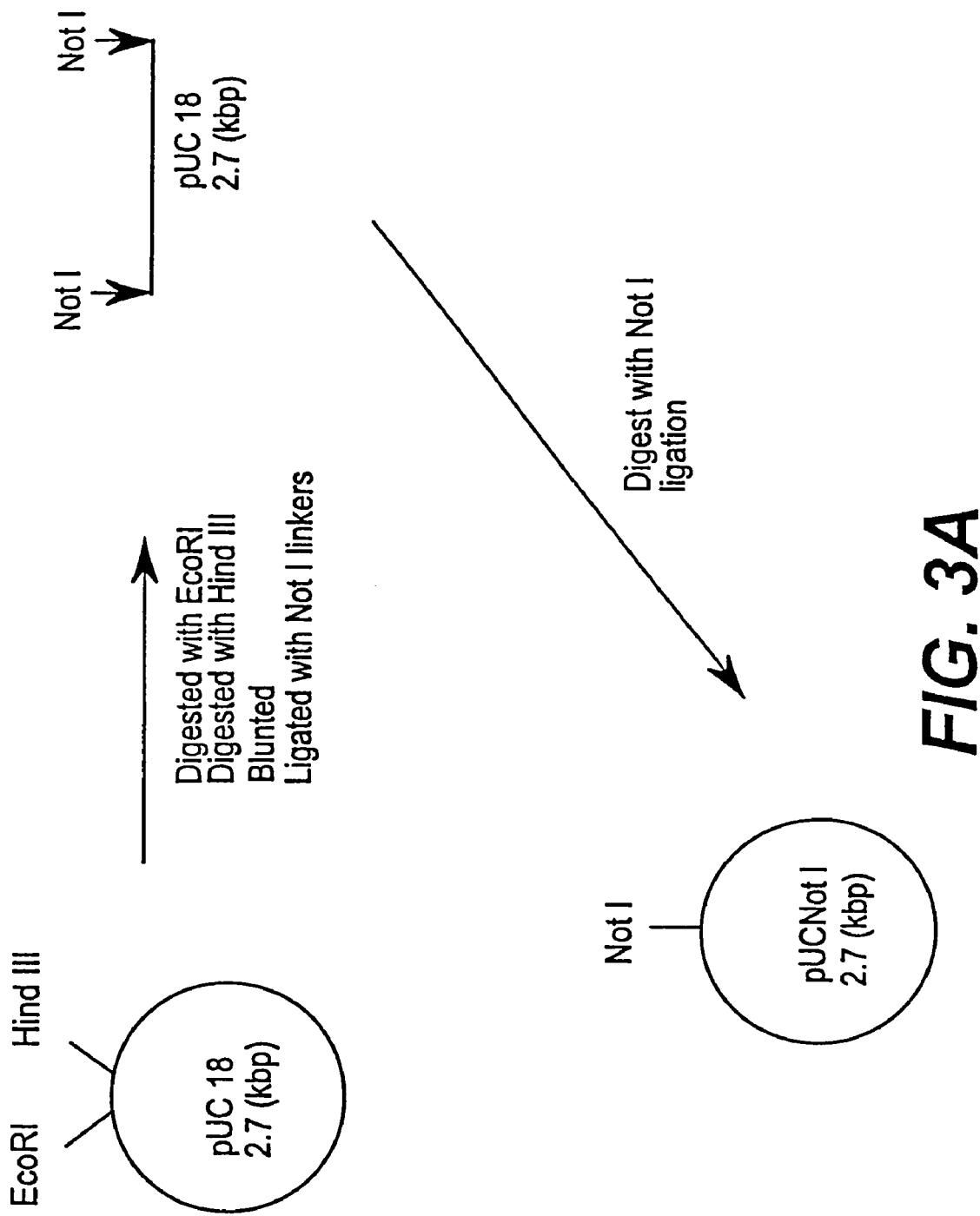
FIGS. 3A-3C show the production of the pUCWAP6 "cassette vector." Specifically.
Figure 3B:
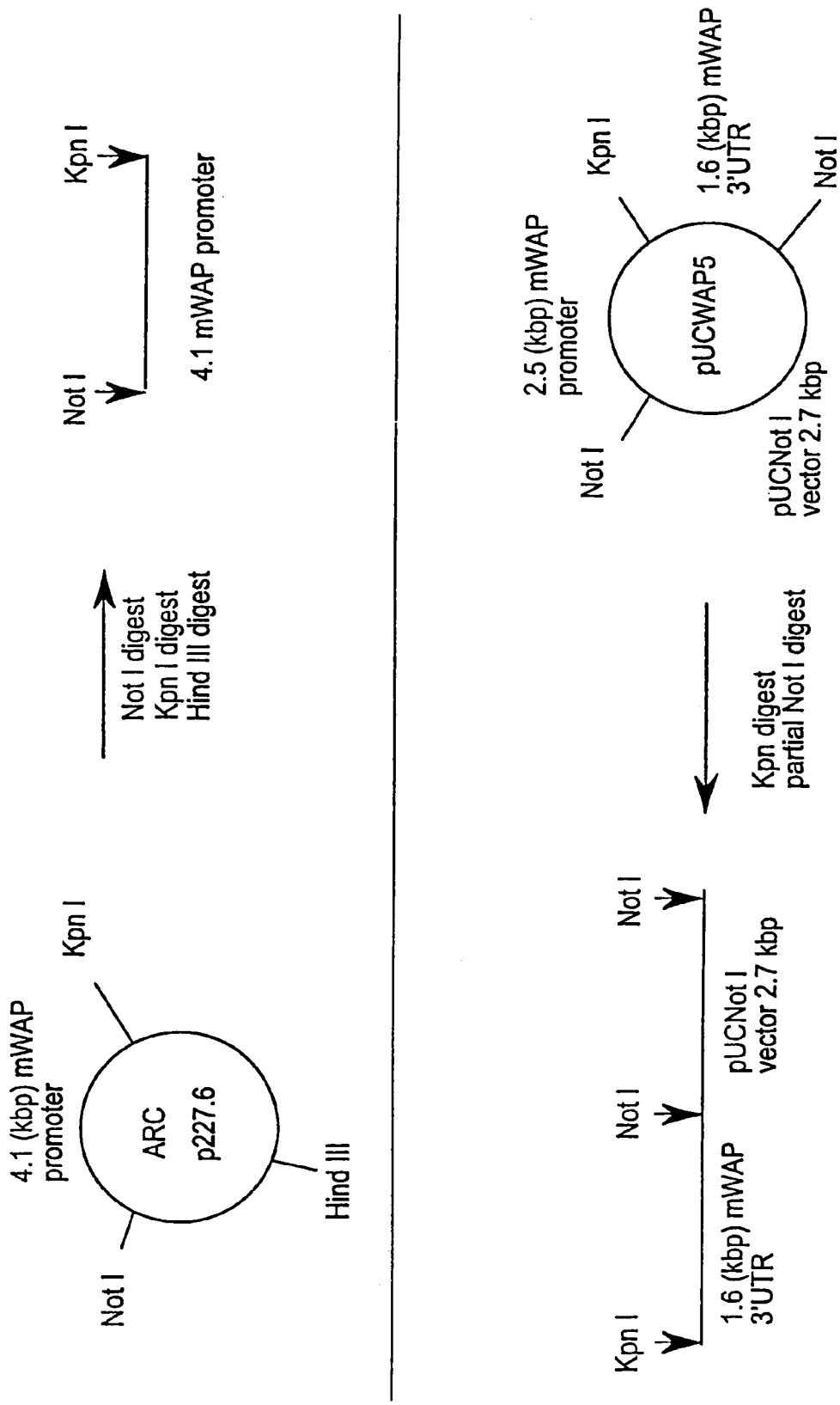
Figure 3C:
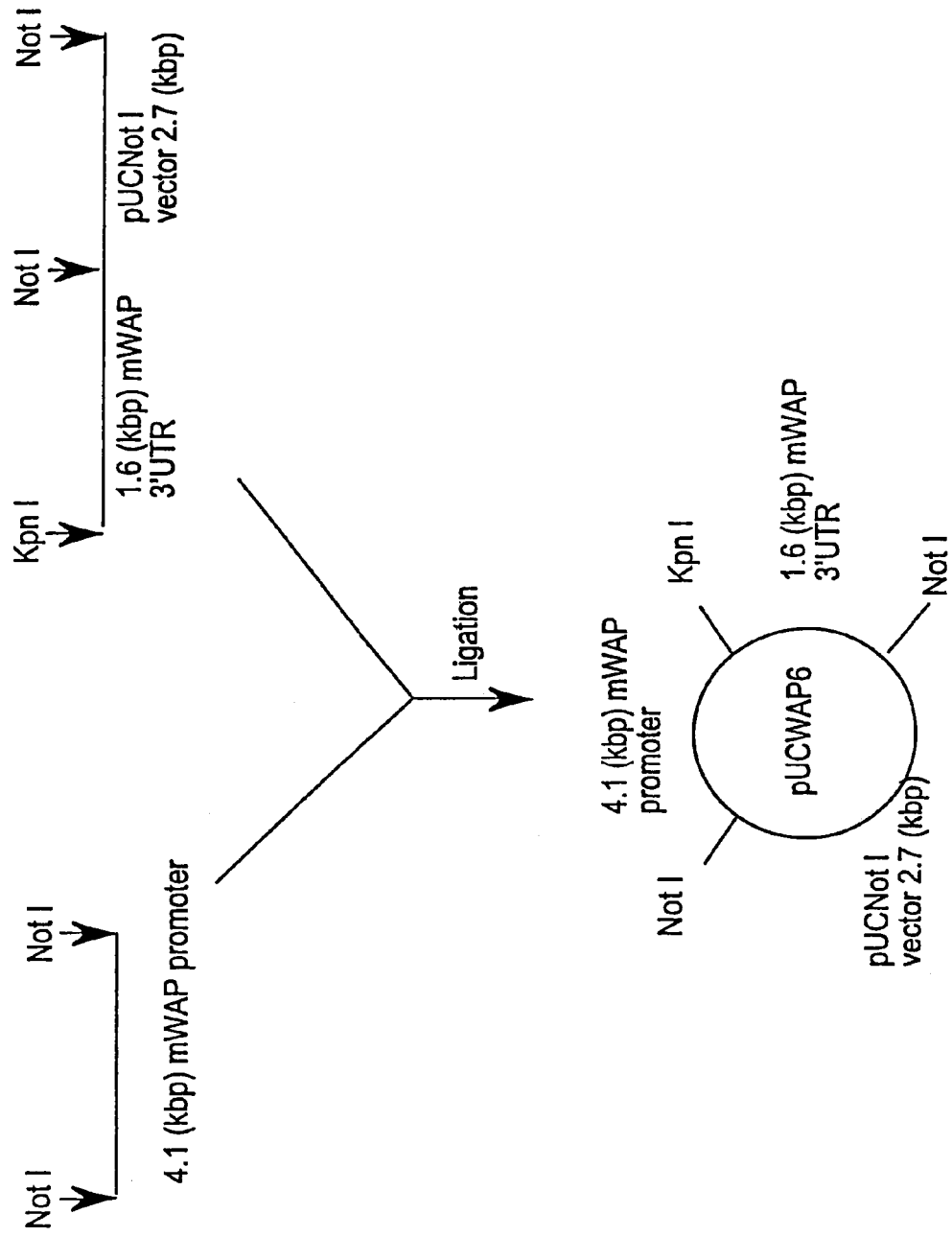

The vector designated pUCWAP6 was derived from genetic elements from the following plasmids as starting material: pUC18, pWAP4 and p227.6, which were provided by the American Red Cross. The development of pUCWAP6 is as follows: The pUC18 vector was cut with the enzymes EcoRI and Hind III to remove the multiple cloning site of the vector, blunted with exonuclease and ligated with NotI linkers. The linearized plasmid was then cut with NotI and ligated. Ligation mixture was used to transform E. coli DH5α cells on LB ampicillin plates, picked colonies were grown in TB ampicillin broth, plasmids were isolated and cut with NotI then subjected to gel electrophoresis. Plasmid was judged to be correct and designated as pUCNotI (See FIG. 3A). The vector pWAP4 was cut with EcoRI and the fragment containing the WAP 5' 2.6 kbp and 3' genetic elements were separated by gel electrophoresis and purified. The ends of the fragment were modified by blunting with exonuclease and NotI linkers were ligated on. The fragment was cut with NotI and ligated into the NotI restriction site of pUCNotI then used to transform E. coli DH5α cells on ampicillin plates picked colonies were grown in TB ampicillin broth. Isolated plasmid was verified to be correct by NotI digestion with the plasmid being designated pUCWAP5. The pUC WAP5 plasmid was subjected to KpnI digestion and a partial NotI digestion producing a fragment that contained the pUCNotI vector sequence flanked by the mWAP 3'UTR (See FIG. 3B). This fragment was ligated with the 4.1 kb 5' WAP promoter produced from digestion of p227.6 with NotI, KpnI and Hind III. The ligation mixture was then used to transform E. coli JM109 cells that were grown on LB ampicillin plates picked colonies were grown in TB ampicillin broth, plasmids isolated were cut with Not I, and NotI/KpnI and judged to be correct. The plasmid was then designated pUCWAP6 (See FIG. 3C).

Production of pUCWAP6FIX

Figure 4:
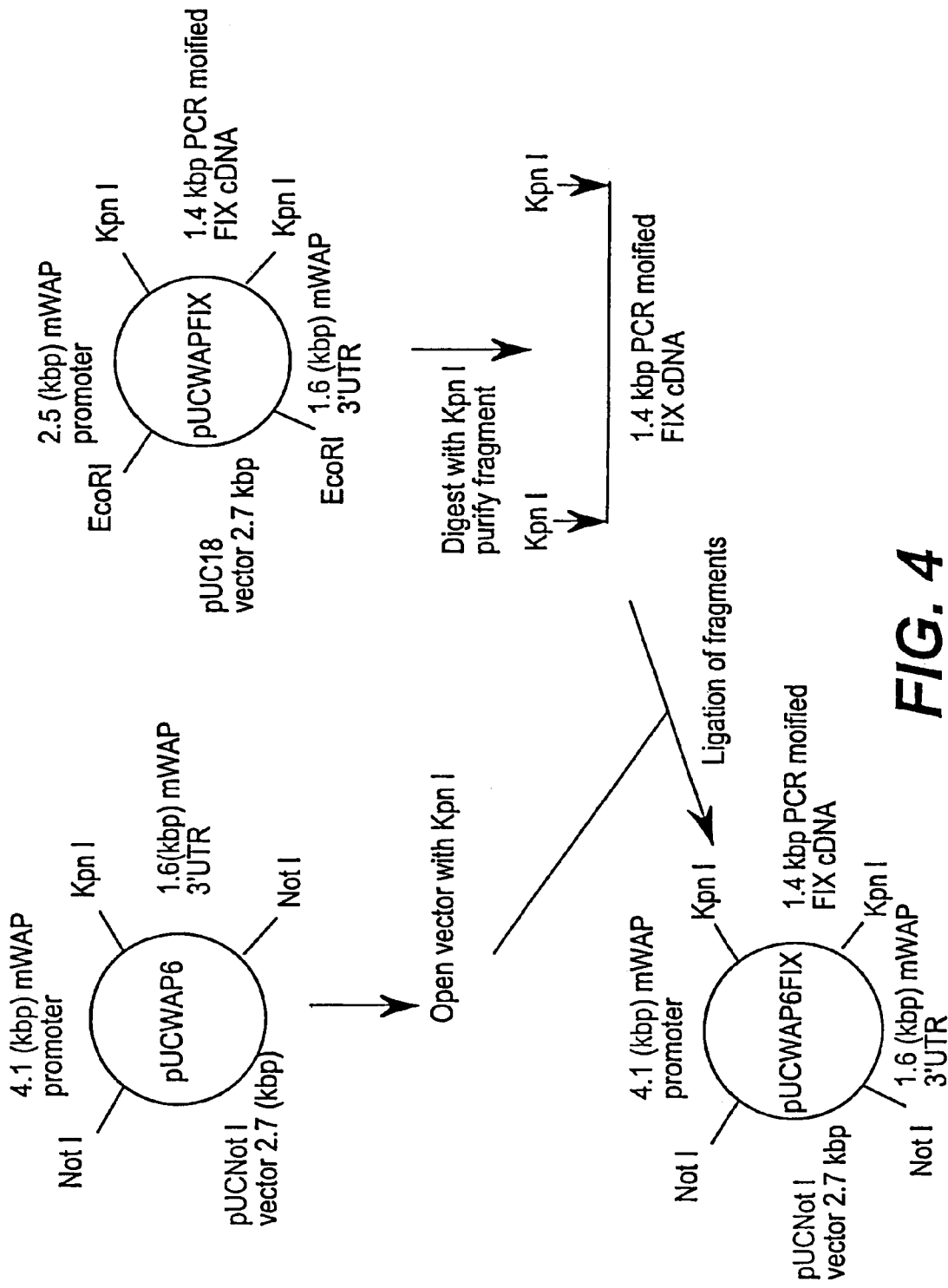
FIG. 4 shows the production of plasmid pUCWAP6FIX.

As shown in FIG. 4, the plasmid pUCWAP6FIX was produced by digestion of pUCWAPFIX with KpnI and isolating the FIX cDNA by gel electrophoresis. This fragment was inserted into the KpnI site of pUCWAP6 after KpnI digestion and both fragments were then subjected to ligation. The ligation mixture was then used to transform E. coli JM109 cells that were then plated on LB ampicillin plates. Picked colonies were grown in TB ampicillin broth and plasmids were isolated. Isolated plasmids were digested with NsiI to verify orientation of the cDNA insert. Plasmids that contained the insert in the correct orientation were designated pUCWAP6FIX. After insert confirmation, large scale purification was undertaken, according to methods well known in the art. DNA was prepared for microinjection as described above.

EXAMPLE 4

Production of Transgenic Mice that Express the Human Factor IX Gene

Transgenic mice were produced essentially as described by Hogan et al., *Manipulating the Mouse Embryo*, Cold Spring Harbor Press, (1986), which is hereby incorporated by reference. That is, glass needles for micro-injection were prepared using a micropipet puller and microforge. Injections were performed using a Nikon microscope having Hoffman Modulation Contrast optics, with Narashigi micromanipulators and a pico-injector driven by N2 (Narashigi).

Fertilized mouse embryos were surgically removed from oviducts of superovulated female CD-1 mice and placed into M2 medium. Cumulus cells were removed from the embryos with hyaluronidase at 300 μg/ml. The embryos were then rinsed in new M2 medium, and transferred into M15 medium for storage at 37 degrees centigrade prior to injection.

Stock solutions containing about 1.4 µg/ml of the above described DNA were prepared and microinjected into the pronuclei of 1 cell mouse embryos. In addition, stock solutions containing about 7 µg/ml total DNA were prepared and microinjected into the pronuclei of mouse embryos.

After injecting the DNA solution into the male pronucleus, embryos were implanted into avertin-anesthesized CD-1 recipient females made pseudo-pregnant by mating with vasectomized males. About 25-30 microinjected mouse embryos per recipient were transferred into pseudopregnant females. Embryos were allowed to come to term and the newborn mice were analyzed for the presence of the transgene by PCR using the primers FIXS1 and FIXA1 described in Table 1, below.

EXAMPLE 5

Preparation of DNA from Transgenic Animals

DNA can be prepared from tissue of a transgenic animal of any species by the method exemplified below for mice. Marmur., *J. Mol. Biol.* 3: 208 (1961), incorporated herein by reference.

A 5 mm piece of mouse tail was removed from young, potentially transgenic mice at weaning (3 weeks) age, and frozen in liquid nitrogen. To the frozen tissue was added 840 µl of Lysing Solution (8 mM EDTA-0.8% 2-mercaptoethanol-80 µg/ml Proteinase K-1 M sodium chlorate in 40 mM TRIS buffer) pH 8.0 and 120 mM NaCl, and the mixture incubated at 50 degrees centigrade. The mixture was then extracted with 250 µl of phenol/chloroform-/isoamyl alcohol (25:24:1) for 10-15 seconds, then centrifuged for 10 minutes. The supernatant fluid (about 830 µl) was removed to a fresh tube, and a DNA clot produced by vortexing the solution with 0.6 vols. of isopropanol. The mother liquor was decanted, and the DNA clot rinsed twice with 80% ethanol. The DNA clot was isolated by 5 minutes or centrifugation, aspiration of the supernatant fluid, and air drying of the clot with a stream of air for 10 minutes.

The DNA clot was dissolved in 250 µl of the TE buffer (10 mM Tris. HCl, pH 7.0-1 mM EDTA, and the solution treated with 10 µl of RNase (1 mg/ml RNase A and 4,0000 units/ml RNAse T1) for 1 hour at 37 degrees centigrade. This mixture was shaken with 50 µl of a 24:1 (v/v) solution of chloroformisoamyl alcohol for 5-10 seconds, centrifuged, and the supernatant fluid transferred to a fresh tube.

The recovered supernatant fluid above was mixed sequentially with 25 µl of 3M sodium acetate and 0.5 ml of 95% ethanol. The supernatant fluid above was mixed sequentially with 25 µl of 3M sodium acetate and 0.5 ml of 95% ethanol. The supernatant fluid was decanted from the precipitated DNA, and the precipitate washed with 80% ethanol. The purified DNA was isolated by centrifugation, air dried, then dissolved in 150 µl of TE.

Essentially the same technique was used to prepare DNA from pigs, and the same or similar techniques can be used to prepare DNA from other animals. Such DNA can be analyzed to determine whether transgenic animals carried recombinant structures.

EXAMPLE 6

Analysis of DNA Derived from Tissue

To determine whether test animals carried the recombinant constructs, tissue samples were removed from transgenic animals and treated with proteinase K and SDS at 37° C. overnight. The mixture was then incubated with DNase-free RNase at 37° C. for 1-2 hours. DNA was precipitated from the mixture with sodium acetate and ethanol at −20° C. overnight, collected by centrifugation, washed in 70% ethanol and dried. The dried DNA pellet was used directly for polymerase chain reaction (PCR). In some cases, the mixture was extracted extensively with phenol/chloroform prior to ethanol precipitation.

Oligonucleotide pairs were used to prime polymerase chain reactions that detected the presence of the WAP gene or the Factor IX gene in the transgenic animals. See Table 1, below. Reactions were performed using an annealing temperature of 58° C., a denaturation temperature of 94° C., and an extension temperature of 72° C., using 100 ng of oligo primers and 50 ng of (genomic) template DNA per reaction, and cycling through the temperatures 40 times using an automatic temperature cycler (M.J. Research). PCR reactions were analyzed by running 20% of the reaction products on agarose gels and identifying fragment sizes by comparison with marker DNA fragments.

Two founder transgenic pigs (one male and one female) contained a 2.6 kb mouse WAP promoter-Factor IX cDNA-1.6 kb WAP gene 3'-end construct that had been coinjected with the 7.2 kb mouse WAP gene (EcoRI-EcoRI) fragment. As shown in Table 2, the male, 57-7, did not transmit the transgene. In contrast, founder 58-1 huas produced one female offspring having the Factor IX cDNA transgene. Founder 58-1 has produced six additional offspring, three females and three males, from her second litter. The three females were not transgenic. Two of the males from the second litter tested positive for the Factor IX transgene.

TABLE 1

Primer Sequences

| | | |
|---|---|---|
| humFIX5' KpnI | (SEQ ID NO:1) | 5'gcta\ggtacc\atgcagcgcg |
| humFIX3' KpnI | (SEQ ID NO:2) | 5'gtca\ggtacc\ttaagtgagct |
| FIXS1 | (SEQ ID NO:3) | 5'ggataacatcactcaaagcac |
| WAP3'A1 | (SEQ ID NO:4) | 5'tagcagcagattgaaagcattatg |
| FIXA1 | (SEQ ID NO:5) | 5'gtgaactttgtagatc |

TABLE 2

Transgenic Pigs Containing Recombinant Human Factor IX DNA

| Pig ID | Construct | Sex | Comments |
|---|---|---|---|
| 57-7 | WAP/FIX | Male | Founder, PCR* positive for WAP and FIX |
| 58-1 | WAP/FIX | Female | Founder, PCR positive for WAP and FIX |
| 63-1 | WAP/FIX | Female | G$^1$ from 58-1, positive for WAP and FIX |
| 63-2 | WAP/FIX | Female | G$^1$ from 58-1, positive for WAP and FIX (dead) |
| litter#10 to 58-1 | WAP/FIX | 3Female, 3Male | 2 transgenic males |

WAP: Whey acid protein; FIX: Factor IX;
*Detection of human Factor IX transgene carried out by the PCR method.

EXAMPLE 7

Expression of Human Factor IX in the Milk of Transgenic Pigs

Daily expression levels of recombinant human Factor IX in the milk of transgenic pig 58-1 were determined as follows. Lactating sows were injected intramuscularly with 30-60 IU of oxytocin (Vedco Inc., St. Joseph, Mo.) to stimulate milk let-down. Letdown occurred two to five minutes after injection. Pigs were milked by hand during the course of this study. Immediately after collection the milk was diluted 1:1 with 200 mM EDTA, pH 7.0 to solubilize the caseins and then frozen. Small aliquots (about one milliliter) of the milk/EDTA mixture were taken and centrifuged for approximately 30 minutes at 16000×g at 4° C. The fat layer was separated from the diluted whey fraction, and the diluted whey fraction was used for all further assays. In this study, all concentration values reported for milk were obtained from diluted whey samples that were multiplied by a factor of 1.9 to account for dilution with EDTA and subsequent removal of milk fat.

Amounts of Factor IX in milk were measured by polyclonal ELISA. Briefly, Immulon II microtiter plates (Fisher Scientific, Pittsburgh) were coated overnight with 100 μl/well of 1:1000 rabbit anti-human Factor IX (Dako) in 0.1 M $NaHCO_3$, 0.1 M NaCl, pH 9.6 at 4° C. The wells were washed with TBS-Tween (TBST, 25 mM Tris, 50 mM NaCl, 0.2% Tween 20, pH 7.2), and then blocked for 30 minutes with TBS/0.1% BSA at room temperature. Samples and human Factor IX standard (a gift from the American Red Cross) in the TBS-BSA dilution buffer were added in triplicate to the wells (100 μl/well) and incubated at 37° C. for 30 minutes. The wells were then washed and blocked for another 10 minutes at room temperature. Goat anti-human Factor IX (American Diagnostica, Greenwich, Conn.), 1:1000 in TBS-BSA, was then incubated in the wells for 30 minutes at 37° C., followed by anti-goat IgG/HRP (Sigma, St. Louis). Bound chromophore was detected with OPD substrate (Abbott, Chicago) at 490 nm using an EL308 Bio-Tek Microplate reader.

As shown in Table 3, daily expression levels of 100-220 μg/ml milk were maintained throughout the 10 day lactation.

TABLE 3

Recombinant Factor IX Levels in Milk of Transgenic Pig 58-1, First Lactation

| Day of Lactation | rhFIX Level[2] [μg/ml] |
|---|---|
| 3 | 160 ± 26 |
| 4 | 145 ± 20 |
| 5 | 100 ± 25 |
| 6 | 135 ± 15 |
| 7 | 220 ± 30 |
| 9 | 170 ± 35 |
| 10 | 185 ± 50 |

[2]Recombinant human Factor IX (rhFIX) levels were determined by ELISA on daily samples of EDTA-diluted whey.

EXAMPLE 8

Western Analysis of Human Factor IX Produced by Transgenic Pigs

Recombinant human Factor IX also was examined using Western analysis. Daily samples of EDTA-diluted whey from 58-1 were electrophoresed on 8-16% SDS gels (Novex, San Diego). Approximately 125 ng of recombinant human Factor IX (as determined by polyclonal ELISA) and human Factor IX standard (American Red Cross), were loaded in each lane. A total of 25 μg of total protein from a pool of non-transgenic (NTG) whey was loaded on the gels. After electrophoresis, proteins were transferred overnight to PVDF membranes (Bio Rad). The membranes were washed for 30 minutes in TBST, blocked with TBS/0.05% Tween 20/0.5% Casein (TBST-Casein). The membranes were developed with rabbit anti-Factor IX (Dako) (1:1000 in TBST-Casein for 45 minutes at 37° C.), followed by anti-rabbit IgG/HRP (Sigma) (1:1000 in TBST-Casein for 45 minutes at 37° C.), and the DAB metal enhanced staining (Pierce). Molecular weight markers were purchased from Bio Rad.

Western analyses revealed the presence of three sub-populations of recombinant human Factor IX: the major population migrated at a $M_r$ of about 60-65 kDa, which is a slightly lower $M_r$ than human Factor IX, and minor sub-populations migrated at about 40-45 kDa, and at about 25 kDa. Plasma human Factor IX also possessed a subpopulation at about 45-50 kDa.

Figure 2:
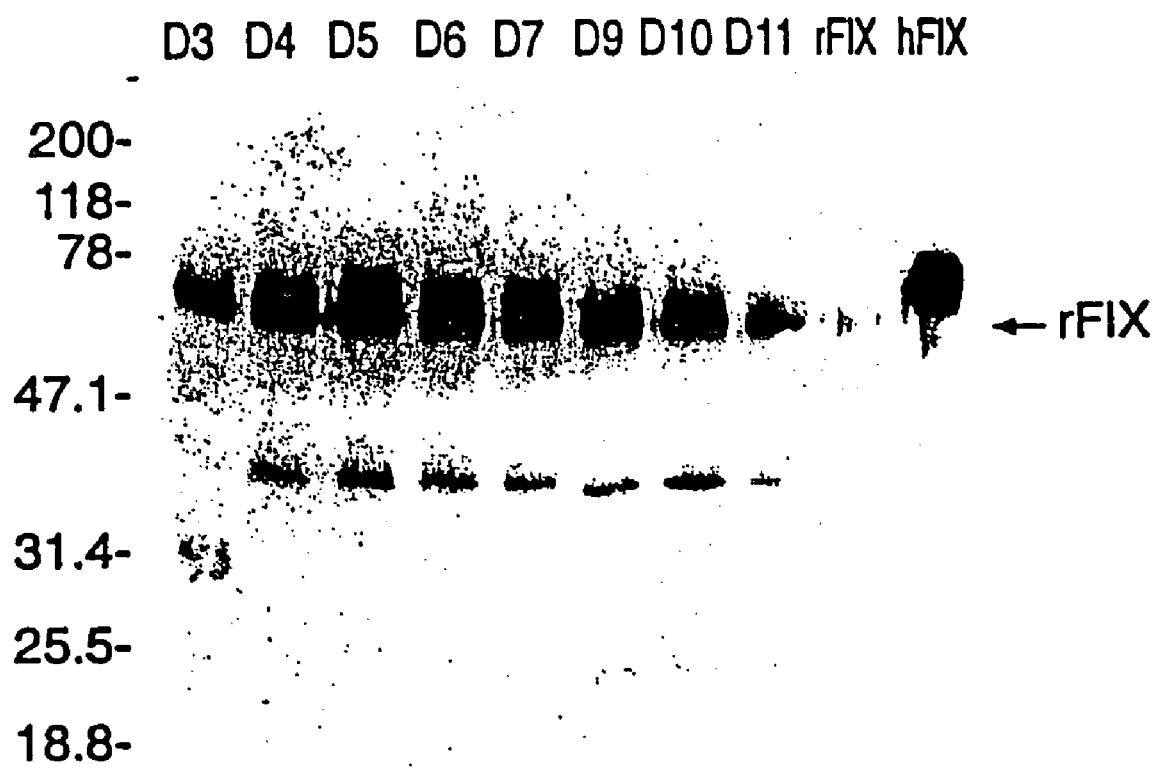
FIG. 2 shows the detection of recombinant Factor IX in transgenic pig milk using western blot analysis.

In yet another study, whole milk from transgenic pig 58-1 was diluted 1:1 with 200 mM EDTA, pH 7.0 to dissociate casein micelles. Milk was skimmed of fat by centrifugation at 4000×g for 30 min, at 2° C. 100 μgs of milk protein were loaded per lane of a 4%/10% SDS-PAGE gel and resolved at 15 mA/hr for one hour and 30 mA/hr for 2 hours. Proteins were transferred onto nitrocellulose paper (Amersham), at 24 V/h, 40° C. and western blotted to detect rFIX in milk, using an HRP-conjugated goat anti-FIX antibody (Affinity Biologicals) at 0.9 μg/ml concentration. The results of this study are set forth in FIG. 2, wherein lanes 1-8 represent milk from day 3, 4, 5, 6, 7, 9, 10, 11 of lactation; lane 9, purified recombinant FIX, 1.0 μg; and lane 10, human FIX purified from plasma, 0.5 μg. The positions of broad range molecular weight markers (BioRad) are indicated on the left.

EXAMPLE 9

Purification of Human Factor IX from Milk of Transgenic Pigs

Recombinant human Factor IX was purified from a pool of the first lactation from the milk of 58-1 using ion exchange chromatography followed by metal-dependent immunoaffinity chromatography (MAb 1H5). In these studies, all columns and buffers were kept at 4° C. A pool of daily EDTA-expanded whey samples was diluted to OD 280 nm of 5.0 with TBS, pH 7.2, then loaded at 1 cm/min on DEAE FF Sepharose. The column was washed with TBS, pH 7.2, and then eluted with 0.25 M NaCl in TBS. This fraction was diluted 1:1 with 40 mM $MgCl_2$ in TBS to a final concentration of 20 mM $MgCl_2$ and loaded on a 1H5 MAb column. The column was washed with TBS containing 20 mM $MgCl_2$, and the product was eluted with 20 mM citrate, 0.15 M NaCl, pH 6.8. The product was dialyzed overnight against 10 mM imidazole, pH 7.2.

The yields from the anion exchange and immunoaffinity steps were quantitative, and no recombinant human Factor IX was detected in the flow-through chromatographic fractions by polyclonal ELISA. This two-step chromatographic procedure isolated the recombinant human Factor IX to about 80-90% purity.

EXAMPLE 10

The Biological Activity of Purified Recombinant Human Factor IX

The biological activity of the purified recombinant human Factor IX from 58-1 was measured using a one-stage activated partial thromboplastin clotting time assay (APTT) clotting assay following a protocol given by the American Red Cross Plasma Derivatives Laboratory (Procedure for Factor IX Coagulation Assay, March 1992). Briefly, each well of a plastic Coag-a-mate tray received 90 µl of Factor IX-deficient plasma plus 10 µl of a Factor IX standard or sample, diluted with Tris/saline/BSA. The tray was then placed on an automated analyzer (APTT mode, 240 second activation). The run was started, which automatically performed the addition of 100 µl of APTT reagent and 100 µl of 0.025 M CaCl$_2$. Data obtained using a standard Factor IX preparation were fitted to the equation y=ax+b where y=clotting time and x=Factor IX, which was then used to determine the amount of Factor IX in a sample. The Standards of normal plasma reference pool (Sigma) and human Factor IX (American Red Cross Plasma Derivatives Laboratory) were used in the assay. Duplicates of 58-1 recombinant human Factor IX, human Factor IX, and normal plasma reference pool samples were run at each dilution.

As shown in Table 4, the immunopurified recombinant human Factor IX had a specific activity of 337 U/mg, which is comparable to the immunopurified human Factor IX from plasma which had a specific activity of 230 U/mg, and the normal plasma reference pool activity of 250 U/mg.

TABLE 4

Specific Activity of Recombinant Human Factor IX Purified from the Milk of a Transgenic Pig

| Sample | Slope | Slope Ratio | Equation | Activity (%) | Specific Activity |
|---|---|---|---|---|---|
| NPRP | 0.094 | 1.0 | y = 0.094x − 3.7 | 100% | 250 U/mg |
| hFIX | 0.086 | 0.92 | y = 0.086x − 3.6 | 92% | 230 U/mg |
| rhFIX | 0.127 | 1.35 | y = 0.127x − 3.4 | 135% | 337 U/mg |

NPRP: normal plasma reference pool
hFIX: human Factor IX standard
rhFIX: Factor IX isolated from the transgenic pig Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A method of treating a patient having hemophilia B comprising administering to said patient a hemophilia B symptom preventing or ameliorating amount of a biologically active human Factor IX produced by a transgenic pig that secretes the biologically active human Factor IX into its milk, and wherein said transgenic pig comprises stably integrated into its genome an exogenous DNA molecule encoding said biologically active human Factor IX; and a pharmaceutically acceptable carrier.

2. The method of claim 1, wherein said biologically active human Factor IX has a specific activity that is at least about 15-50% greater than the specific activity of human Factor IX isolated from human plasma.

3. The method of claim 1, wherein said transgenic pig secretes at least 100 µg of biologically active human Factor IX per milliliter of milk.

4. The method of claim 1, wherein said amount of said human Factor IX that is administered comprises about 18-30 IU/kg administered once a week.

5. The method of claim 1, wherein said administration of said human Factor IX raises Factor IX levels 20% or greater in the blood.

6. A purified or isolated biologically active human Factor IX produced in a transgenic pig which secretes said biologically active human Factor IX into its milk, wherein said transgenic pig comprises stably integrated into its genome an exogenous DNA molecule encoding said biologically active human Factor IX.

7. The biologically active human Factor IX of claim 6, wherein said biologically active human Factor IX comprises a specific activity that is at least about 15-50% greater than the specific activity of human Factor IX isolated from human plasma.

8. The biologically active human Factor IX of claim 6, wherein said transgenic pig secretes at least 100 µg of biologically active human Factor IX per milliliter of milk.

9. The biologically active human Factor IX of claim 6, wherein said biologically active human Factor IX comprises a sufficiently γ-carboxylated, biologically active Factor IX.

10. The biologically active human Factor IX of claim 6, wherein said biologically active human Factor IX further comprises a pharmaceutically acceptable carrier.

11. The method of claim 1, wherein said amount of said human Factor IX that is administered comprises about 9-15 IU/kg administered twice a week.

12. The method of claim 1, wherein said administration of said human Factor IX raises Factor IX levels to 50% in the blood.

13. The method of claim 1, wherein said biologically active human Factor IX is isolated or purified from said milk.

* * * * *

UNITED STATES PATENT AND TRADEMARK OFFICE
CERTIFICATE OF CORRECTION

PATENT NO. : 7,419,948 B2
APPLICATION NO. : 11/117705
DATED : September 2, 2008
INVENTOR(S) : Velander et al.

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 88 days Delete the phrase "by 88 days" and insert -- by 214 days --

Signed and Sealed this

Fifteenth Day of June, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 20
<212> TYPE: DNA
<213> ORGANISM: Homo sapiens

<400> SEQUENCE: 1
gctaggtacc atgcagcgcg                                          20

<210> SEQ ID NO 2
<211> LENGTH: 21
<212> TYPE: DNA
<213> ORGANISM: Homo sapiens

<400> SEQUENCE: 2
gtcaggtacc ttaagtgagc t                                        21

<210> SEQ ID NO 3
<211> LENGTH: 21
<212> TYPE: DNA
<213> ORGANISM: Homo sapiens

<400> SEQUENCE: 3
ggataacatc actcaaagca c                                        21

<210> SEQ ID NO 4
<211> LENGTH: 24
<212> TYPE: DNA
<213> ORGANISM: Murine

<400> SEQUENCE: 4

```
tagcagcaga ttgaaagcat tatg                                              24

<210> SEQ ID NO 5
<211> LENGTH: 16
<212> TYPE: DNA
<213> ORGANISM: Homo sapiens

<400> SEQUENCE: 5
gtgaactttg tagatc                                                       16
```